United States Patent [19]
Hlavinka

[11] Patent Number: 6,053,856
[45] Date of Patent: Apr. 25, 2000

[54] TUBING SET APPARATUS AND METHOD FOR SEPARATION OF FLUID COMPONENTS

[75] Inventor: Dennis Hlavinka, Arvada, Colo.

[73] Assignee: Cobe Laboratories, Lakewood, Colo.

[21] Appl. No.: 08/853,374

[22] Filed: May 8, 1997

Related U.S. Application Data

[63] Continuation-in-part of application No. 08/423,578, Apr. 18, 1995, Pat. No. 5,674,173, and application No. 08/423,583, Apr. 18, 1995, abandoned.

[51] Int. Cl.$^7$ .............................. B01D 21/26; B04B 7/08
[52] U.S. Cl. .............................. 494/37; 210/782; 494/36; 494/38; 494/45
[58] Field of Search ................................... 210/782, 787, 210/789, 252, 259, 360.1; 494/36, 37, 38, 45; 604/4, 5, 6

[56] References Cited

U.S. PATENT DOCUMENTS

| | | |
|---|---|---|
| 1,684,870 | 9/1928 | Lewis . |
| 2,616,619 | 11/1952 | MacLeod . |
| 2,878,995 | 3/1959 | Dega . |

(List continued on next page.)

FOREIGN PATENT DOCUMENTS

| | | |
|---|---|---|
| 0 363 120 | 2/1989 | European Pat. Off. . |
| 0 406 485 A1 | 1/1991 | European Pat. Off. . |
| 0 408 462 A2 | 1/1991 | European Pat. Off. . |
| 0 419 346 A2 | 3/1991 | European Pat. Off. . |
| 26 58 926 | 12/1976 | Germany . |
| 37 00 122 | 7/1988 | Germany . |
| WO 94/02157 | 2/1994 | WIPO . |
| WO 94/27698 | 12/1994 | WIPO . |
| WO 96/33023 | 10/1996 | WIPO . |
| WO 96/40402 | 12/1996 | WIPO . |
| WO 97/30748 | 8/1997 | WIPO . |

OTHER PUBLICATIONS

A. Plas et al., "A New Multichamber Centrifugation Rotor with High–separation Capacity and Versatile Potentials;" Exp. Hematol. 16:355–359 (1988).

M. Kaufman et al., "Isolation of Cell Cycle Fractions by Counterflow Centrifugal Elutriation;" Analytical Biochemistry 191, 41–46 (1990).

A. Faradji et al., "Large Scale Isolation of Human Blood Monocytes by Continuous Flow Centrifugation Leukapheresis and Counterflow Centrifugation Elutriation for Adoptive Cellular Immunotheraphy in Cancer Patients;" Journal of Immunological Methods 174 (1994) 297–309.

Gao et al., "Implementation of a Semiclosed Large Scale Counterflow Centrifugal Elutriation System;" Journal of Clinical Apheresis 3:514–160 (1987).

Griffith, "Separation of T and B Cells from Human Peripheral Blood by Centrifugal Elutriation;" Analytical Biochemistry 87, 97–107 (1978).

Figdor et al.; "Isolation of Functionally Different Human Monocytes by Counterflow Centrifugation Elutriation;" Blood, vol. 60, No. 1 (Jul.) 1982.

Maxim D. Persidsky et al., Separation of Platelet–Rich Plasma by Modified Centrifugal Elutriation; Journal of Clinical Apheresis 1:18–24 (1982).

John F. Jemionek et al., Special Techniques for the Separation of of Hemopoietic Cells, Current Methodology in Experimental Hematology, 1984, pp. 12–16, Karger, New York.

Primary Examiner—John Kim
Attorney, Agent, or Firm—Finnegan, Henderson, Farrabow, Garrett & Dunner L.L.P.

[57] ABSTRACT

An apparatus and method are provided for separating components of a fluid or particles. A separation vessel having a barrier dam is provided to initially separate an intermediate density components of a fluid, and a fluid chamber is provided to further separate these the intermediate density component by forming an elutriative field or saturated fluidized particle bed. The separation vessel is placed in a retainer on a centrifuge rotor and ridges in the retainer form various dams in the separation vessel. Also discloses are tubing sets and various separation vessels for use with the apparatus.

48 Claims, 9 Drawing Sheets

U.S. PATENT DOCUMENTS

| | | |
|---|---|---|
| 3,771,715 | 11/1973 | Baram . |
| 3,823,869 | 7/1974 | Loison . |
| 3,825,175 | 7/1974 | Sartory . |
| 4,010,894 | 3/1977 | Kellogg et al. . |
| 4,091,989 | 5/1978 | Schlutz . |
| 4,094,461 | 6/1978 | Kellogg et al. . |
| 4,146,172 | 3/1979 | Cullis et al. . |
| 4,187,979 | 2/1980 | Cullis et al. . |
| 4,268,393 | 5/1981 | Persidsky et al. . |
| 4,269,718 | 5/1981 | Persidsky . |
| 4,316,576 | 2/1982 | Cullis et al. . |
| 4,322,298 | 3/1982 | Persidsky . |
| 4,350,283 | 9/1982 | Leonian . |
| 4,356,958 | 11/1982 | Kolobow et al. . |
| 4,386,730 | 6/1983 | Mulzet . |
| 4,387,848 | 6/1983 | Kellogg et al. . |
| 4,413,771 | 11/1983 | Rohde et al. . |
| 4,413,772 | 11/1983 | Rohde et al. . |
| 4,416,654 | 11/1983 | Schoendorfer et al. . |
| 4,419,089 | 12/1983 | Kolobow et al. . |
| 4,421,503 | 12/1983 | Latham, Jr et al. ................ 494/17 |
| 4,425,112 | 1/1984 | Ito . |
| 4,447,221 | 5/1984 | Mulzet . |
| 4,464,167 | 8/1984 | Schoendorfer et al. . |
| 4,610,846 | 9/1986 | Martin . |
| 4,647,279 | 3/1987 | Mulzet et al. . |
| 4,675,117 | 6/1987 | Neumann et al. . |
| 4,680,025 | 7/1987 | Kruger et al. ................ 604/6 |
| 4,701,267 | 10/1987 | Watanabe et al. . |
| 4,708,710 | 11/1987 | Dunn, Jr. . |
| 4,708,712 | 11/1987 | Mulzet . |
| 4,798,579 | 1/1989 | Penhasi . |
| 4,808,151 | 2/1989 | Dunn, Jr. et al. . |
| 4,846,974 | 7/1989 | Kelley et al. . |
| 4,851,126 | 7/1989 | Schoendorfer ................ 210/651 |
| 4,885,137 | 12/1989 | Lork . |
| 4,933,291 | 6/1990 | Daiss et al. . |
| 4,934,995 | 6/1990 | Cullis . |
| 4,936,820 | 6/1990 | Dennehey et al. . |
| 4,936,998 | 6/1990 | Nishimura et al. . |
| 4,939,081 | 7/1990 | Figdor et al. . |
| 4,939,087 | 7/1990 | Van Wie et al. . |
| 5,006,103 | 4/1991 | Bacehowski et al. . |
| 5,078,671 | 1/1992 | Dennehey et al. . |
| 5,089,146 | 2/1992 | Carmen et al. . |
| 5,100,564 | 3/1992 | Pall et al ................ 210/782 |
| 5,203,999 | 4/1993 | Hugues . |
| 5,213,970 | 5/1993 | Lopez-Berestein et al. . |
| 5,217,427 | 6/1993 | Cullis . |
| 5,224,921 | 7/1993 | Dennehey et al. . |
| 5,229,012 | 7/1993 | Pall et al. . |
| 5,282,982 | 2/1994 | Wells . |
| 5,298,171 | 3/1994 | Biesel . |
| 5,316,666 | 5/1994 | Brown et al. . |
| 5,316,667 | 5/1994 | Brown et al. . |
| 5,360,542 | 11/1994 | Williamson, IV et al. . |
| 5,362,291 | 11/1994 | Williamson, IV . |
| 5,370,802 | 12/1994 | Brown . |
| 5,397,479 | 3/1995 | Kass et al. . |
| 5,409,813 | 4/1995 | Schwartz . |
| 5,437,624 | 8/1995 | Langley ................ 604/4 |
| 5,501,795 | 3/1996 | Pall et al. . |
| 5,547,591 | 8/1996 | Hagihara et al. . |
| 5,571,068 | 11/1996 | Bacehowski et al. . |
| 5,580,465 | 12/1996 | Pall et al. . |
| 5,587,070 | 12/1996 | Pall et al. . |
| 5,607,830 | 3/1997 | Biesel et al. . |
| 5,641,414 | 6/1997 | Brown . |
| 5,674,173 | 10/1997 | Hlavinka et al. . |
| 5,722,926 | 3/1998 | Hlavinka et al. ................ 494/37 |
| 5,729,038 | 3/1998 | Hlavinka ................ 494/45 |

OTHER PUBLICATIONS

J. Freedman et al., White cell depletion of red cell and pooled random–donor platelet concentrates by filtration and residual lymphocyte subset analysis, Transfusion, 1991, vol. 31, No. 5, pp. 433–440.

Nancy M. Heddle et al., The Role of the Plasma From Platelet Concentrates in Transfusion Reactions, The New England Journal of Medicine, vol. 331, No. 10, Sep. 8, 1994, pp. 625–628, 670 and 671.

A. Bruil et al., Asymmetric membrane filters for the removal of leukocytes from blood, Journal of Biomed. Materials Research, vol. 25, 1459–1480, 1991.

Sunny Dzik, Leukodepletion Blood Filters: Filter Design and Mechanisms of Leukocyte Removal, Transfusion Medicine Reviews, vol. VII, No. 2, Apr. 1993, pp. 65–77.

Bernard J. Van Wie et al., The Effect of Hematocrit and Recycle on Cell Separations, Plasma Ther. Transfus. Technol. 1986; 7:373–388.

P.D. Drumheller et al., The Effects of RPM and Recycle on Separation Efficiency in a Clinical Blood Cell Centrifuge, Journal of Biomechanical Engineering, Nov. 1987, vol. 109, pp. 324–329.

R. J. Oxford et al., Monitoring and Automated Optimization of a Cell Centrifuge, IEEE/Eighth Annual Conference of the Engineering in Medicine and Biology Society, pp. 925–927.

R. J. Oxford et al., Interface dynamcis in a centrifugal cell separator, Transfusion, Nov.–Dec., 1988, vol. 28, No. 6, pp. 588–592.

A. Tulp et al., A Separation Chamber to Sort Cells and Cell Organelles by Weak Physical Forces. V.A. Sector–Shaped Chamber and Its Application to the Separation of Peripheral Blood Cells, Journal of Immunolgical Methods 69 (1984), pp. 281–295.

Robert J. Grabske, Separating Cell Populations by Elutriation, pp. 1–8 (und

Carl G. Figdor et al., Theory and Practice of Centrifugal Elutriation (CE) Factors Influencing the Separation of Human Blood Cells, Cell Biophysics 5, 105–118 (1983).

P.E. Lindahl, On Counter Streaming Centrifugation in the Separation of Cells and Cell Fragments, pp. 411–415 (undated).

C. Almici et al., Counterflow centrifugal elutriation: present and future, Bone Marrow Transplantation 1993, 12:105–108.

Richard J. Sanderson, Separation of Different Kinds of Nucleated Cells from Blood by Centrifugal Elutriation, Cell Separation Methods and Selected Applications, vol. 1, pp. 153–168.

P.C. Keng et al., Characterization of the Separation Properties of the Beckman Elutriator System, Cell Biophysics 3 (1981), pp. 41–56.

Biofil, Systems for Filtration of Haemocomponents (undated).

Claes F. Hogman, Leukocyte Depletion of Blood Components, 1994 pp. 1, 156–173.

A. S. Buchanan et al., Principle of a Counter–streaming Centrifuge for the Separation of Particles of Different Sizes, Nature, Apr. 24, 1948, pp. 648–649.

"Cost–Effectiveness of Leukocyte Depletion of Blood Components", Presented at the 1993 AABB Meeting Miami Beach, FL.

I. Sniecinski, Prevention of immunologic and infectious complications of transfusion by leukocyte depletion, Prevention of complications of transfusion Chapter 18; pp. 202–211 (undated).

Benefits of Leukocyte Filtration for Red Cell and Platelet Blood Products, Transfusion Associated CMV, pp. 1–18 (1994).

G. Stack et al., Cytokine generation in stored platelet concentrates, Transfusion, 1994; 34:20–25.

N. M. Heddle et al., A prospective study to identify the risk factors associated with acute reactions to platelet and red cell transfusions; Transfusion, 1993; 33:794–797.

H. Brandwein et al., Asahi Sepacell PL10A Leukocyte Removal Filter: Efficiency with Random Donor Platelet Pools, PALL Technical Report (undated).

J. Whitbread et al., Performance Evaluation of the Sepacell PL10A filter and Pall PXL 8 filter: Measurement of Leukocyte Residuals and Consistency, PALL Technical Report (undated).

R. Brown et al., Evaluation of a new separation method utilizing plasma recirculation and autoelutriation, Transfusion, 1994; vol. 34, Supp.

Richard J. Sanderson et al., Design Principles for a Counterflow Centrifugation Cell Separation Chamber; Analytical Biochemistry 71, 615–622 (1976).

Designed to Provide the Reliability and Performance to Harvest a High Yield Component Product, The Haemonetics V50 Apheresis System (undated).

Haemonetics Mobile Collection System Owner's Operating and Maintenance Manual, 1991, pp. 3–2 through 3–7 and pp. 1–6.

E.A. Burgstaler et al., White Blood Cell Contamination of Apheresis Platelets Collected on the COBE Spectra, COBE Blood Component Technology (un T.H. Price et al., Platelet Collection Using the COBE Spectra, COBE Blood Component Technology (1989).

Nancy Besso et al., Asahi Sepacell PL–10A Leukocyte Removal Filter: Effect of Post–Filtration Flush With Saline, PALL Technical Report (1991).

Harvey J. Brandwein et al., Asahi Sepacell PL–10A Leukocyte Removal Filter Description and Review of Claims, PALL Technical Report (1991).

"Lower is Better!", (flyer) PALL Biomedical Products Company (1994).

Judy H. Angelbeck, Adverse Reactions to Platelet Transfusion, Risks and Probable Causes pp. 1–14 (1994).

Centrifugual Elutriation, Beckman pp. 1–7, vi (undated).

As 104 Cell Separator, Fresenius (undated).

CS–3000 Blood Cell Separator, Powerful Technology, Fenwal Laboratories (undated).

Baxter CS–3000 Plus Blood Cell Separator Operator's Manual (7–19–3–136) (undated).

The Mobile Collection System gives you easier access to more donors than ever before, Haemonetics (undated).

LRF6/LRF10, High Efficiency Leukocyte Removal Filter Systems For Platelets PALL Biomedical Products Corporation (undated).

J. Whitbread et al., Reduction of C3A Fragment Levels Following Leukodepletion Using a PALL PXL8 Filter (undated).

T. A. Takahashi et al., Bradykinin Formation in a Platelet Concentrate Filtered with a Leukocyte–removal Filter Made of Nonwoven Polyester Fibers with a Negatively Charged Surface (undated).

Baxter CS–3000 Plus Blood Cell Separator pp. 1–18 (undated).

J.F. Jemionek, Variations in CCE Protocol for Cell Isolation, Elutriation, pp. 17–41 (undated).

Bernard John Van Wie, Conceptualization and Evaluation of Techniques for Centrifugal Separation of Blood Cells: Optimum Process Conditions, Recycle and Stagewise Processing, Dissertation, 1982, pp. 27–58.

Brief Operating Instructions, Fresenius MT AS 104 blood cell separator, 4/6.90(OP) (undated).

English language abstract of SU 1725117 A.

English language abstract of SU 1255136.

English language abstract of SU 1236366.

English language abstract of SU 1091071.

English language abstract of DE 3734170.

Multi Chamber Counterflow Centrifugation System, Dijkstra Vereenigde B.V., 6 pgs (undated).

Baxter CS–3000 Plus Blood Cell Separator, Technology With a Mind You Can Own, 1990.

TUBING SET APPARATUS AND METHOD FOR SEPARATION OF FLUID COMPONENTS

This application is a continuation-in-part of U.S. application Ser. No. 08/423,578, filed on Apr. 18, 1995 (now U.S. Pat. No. 5,674,173, issued on Oct. 7, 1997), and is also a continuation-in-part of U.S. application Ser. No. 08/423,583, filed on Apr. 18, 1995 (now abandoned). The entire disclosures of U.S. patent application Ser. Nos. 08/423,578 and 08/423,583 are incorporated herein by reference.

BACKGROUND OF THE INVENTION

1. Field of the Invention

The present invention relates to a tubing set, apparatus, and method for separating components of a fluid. The invention has particular advantages in connection with separating blood components.

2. Description of the Related Art

In many different fields, liquids carrying particle substances must be filtered or processed to obtain either a purified liquid or purified particle end product. In its broadest sense, a filter is any device capable of removing or separating particles from a substance. Thus, the term "filter" as used herein is not limited to a porous media material but includes many different types of processes where particles are either separated from one another or from liquid.

In the medical field, it is often necessary to filter blood. Whole blood consists of various liquid components and particle components. Sometimes, the particle components are referred to as "formed elements". The liquid portion of blood is largely made up of plasma, and the particle components include red blood cells (erythrocytes), white blood cells (including leukocytes), and platelets (thrombocytes). While these constituents have similar densities, their average density relationship, in order of decreasing density, is as follows: red blood cells, white blood cells, platelets, and plasma. In addition, the particle constituents are related according to size, in order of decreasing size, as follows: white blood cells, red blood cells, and platelets. Most current purification devices rely on density and size differences or surface chemistry characteristics to separate and/or filter the blood components.

Numerous therapeutic treatments require groups of particles to be removed from whole blood before either liquid or particle components can be infused into a patient. For example, cancer patients often require platelet transfusions after undergoing ablative, chemical, or radiation therapy. In this procedure, donated whole blood is processed to remove platelets and these platelets are then infused into the patient. However, if a patient receives an excessive number of foreign white blood cells as contamination in a platelet transfusion, the patient's body may reject the platelet transfusion, leading to a host of serious health risks.

Typically, donated platelets are separated or harvested from other blood components using a centrifuge. The centrifuge rotates a blood reservoir to separate components within the reservoir using centrifugal force. In use, blood enters the reservoir while it is rotating at a very rapid speed and centrifugal force stratifies the blood components, so that particular components may be separately removed. Centrifuges are effective at separating platelets from whole blood, however they typically are unable to separate all of the white blood cells from the platelets. Historically, blood separation and centrifugation devices are typically unable to consistently (99% of the time) produce platelet product that meets the "leukopoor" standard of less than $5 \times 10_6$ white blood cells for at least $3 \times 10_{11}$ platelets collected.

Because typical centrifuge platelet collection processes are unable to consistently and satisfactorily separate white blood cells from platelets, other processes have been added to improve results. In one procedure, after centrifuging, platelets are passed through a porous woven or non-woven media filter, which may have a modified surface, to remove white blood cells. However, use of the porous filter introduces its own set of problems. Conventional porous filters may be inefficient because they may permanently remove or trap approximately 5–20% of the platelets. These conventional filters may also reduce "platelet viability," meaning that once passed through a filter a percentage of the platelets cease to function properly and may be partially or fully activated. In addition, porous filters may cause the release of brandykinin, which may lead to hypotensive episodes in a patient. Porous filters are also expensive and often require additional time consuming manual labor to perform a filtration process.

Although porous filters are effective in removing a substantial number of white blood cells, they have drawbacks. For example, after centrifuging and before porous filtering, a period of time must pass to give activated platelets time to transform to a deactivated state. Otherwise, the activated platelets are likely to clog the filter. Therefore, the use of porous filters is not feasible in on-line processes.

Another separation process is one known as centrifugal elutriation. This process separates cells suspended in a liquid medium without the use of a membrane filter. In one common form of elutriation, a cell batch is introduced into a flow of liquid elutriation buffer. This liquid which carries the cell batch in suspension, is then introduced into a funnel-shaped chamber located in a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

Thus, centrifugal elutriation separates particles having different sedimentation velocities. Stoke's law describes sedimentation velocity (SV) of a spherical particle as follows:

$$SV = \frac{2}{9} \frac{r^2 (\rho_p - \rho_m) g}{\eta}$$

where, r is the radius of the particle, $\rho_p$ is the density of the particle, $\rho_m$ is the density of the liquid medium, $\eta$ is the viscosity of the medium, and g is the gravitational or centrifugal acceleration. Because the radius of a particle is raised to the second power in the Stoke's equation and the density of the particle is not, the size of a cell, rather than its density, greatly influences its sedimentation rate. This explains why larger particles generally remain in a chamber during centrifugal elutriation, while smaller particles are released, if the particles have similar densities.

As described in U.S. Pat. No. 3,825,175 to Sartory, centrifugal elutriation has a number of limitations. In most of these processes, particles must be introduced within a flow of fluid medium in separate discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

Further, a Coriolis jetting effect takes place when particles flow into an elutriation chamber from a high centrifugal field toward a lower centrifugal field. The fluid and particles turbulently collide with an inner wall of the chamber facing the rotational direction of the centrifuge. This phenomenon mixes particles within the chamber and reduces the effectiveness of the separation process. Further, Coriolis jetting shunts flow along the inner wall from the inlet directly to the outlet. Thus, particles pass around the elutriative field to contaminate the end product.

Particle mixing by particle density inversion is an additional problem encountered in some prior elutriation processes. Fluid flowing within the elutriation chamber has a decreasing velocity as it flows in the centripetal direction from an entrance port toward an increased cross sectional portion of the chamber. Because particles tend to concentrate within a flowing liquid in areas of lower flow velocity, rather than in areas of high flow velocity, the particles concentrate near the increased cross-sectional area of the chamber. Correspondingly, since flow velocity is greatest adjacent the entrance port, the particle concentration is reduced in this area. Density inversion of particles takes place when the centrifugal force urges the particles from the high particle concentration at the portion of increased cross-section toward the entrance port. This particle turnover reduces the effectiveness of particle separation by elutriation.

For these and other reasons, there is a need to improve particle separation.

SUMMARY OF THE INVENTION

The present invention is directed to an apparatus and method that substantially obviate one or more of the limitations and disadvantages of the related art. To achieve these and other advantages and in accordance with the purpose of the invention, as embodied and broadly described herein, the invention includes a tubing set for use with a centrifuge. The tubing set has a separation vessel having an inlet end portion including an inlet port for supplying to the vessel a fluid to be separated into components, an outlet end portion including at least a first collection port, a second collection port, and a third collection port for removing separated components of the fluid from the vessel, and a flow path extending between the inlet end portion and the outlet end portion. The tubing set also includes an inlet line and various collection lines. In addition, a fluid chamber is provided for separating components of the fluid after initial separation in the vessel.

In another aspect, the invention includes a centrifugal separation apparatus having a separation vessel including a first wall and a second wall formed of at least one of a flexible material and a semi-rigid material. Inner surfaces of the first and second walls are spaced from one another to define a flow path therebetween for a fluid capable of being separated into components. In an outlet portion, the vessel includes at least one sealed portion wherein the first and second walls are sealed together, the sealed portion being located between top and bottom edges of the vessel to form at least first and second flow passages in the outlet portion, the sealed portion defining at least a portion of a barrier for the at least one separated fluid component when the separation vessel is placed in a retainer on a centrifuge rotor.

In another aspect, the invention includes an apparatus having a rotor and a retainer on the rotor for receiving a separation vessel therein. The retainer includes an inner wall spaced from the axis of rotation and an outer wall spaced further from the axis of rotation than the inner wall, the inner wall and the outer wall defining a groove therebetween. A first ridge extends from one of the inner wall and the outer wall, and a second ridge extends from the other of the inner wall and the outer wall. The first and second ridges are positioned across from one another and the first ridge is above the second ridge, so that when the separation vessel is placed in the retainer, the first ridge and second ridge form a barrier for substantially blocking passage of predetermined particles in the vessel while allowing passage of other particles and liquid.

In another aspect, a trap dam is provided between a collection port and the inlet portion. The trap dam extends away from the axis of rotation to trap a portion of a low density substance along an inner portion of the vessel.

In another aspect, the invention includes an apparatus including the separation vessel and fluid chamber on a rotor.

In another aspect, the invention includes a method of separating at least first and second particles, the first particles being less dense than the second particles. The method includes blocking passage of at least the first particles in a vessel with a barrier while allowing at least some of liquid and second particles to flow past the barrier, removing via a collection port the blocked first particles and at least some of the second particles and the liquid, passing the first particles, the second particles, and the liquid from the collection port to a fluid chamber, forming a saturated fluidized particle bed of the first particles in the fluid chamber, and filtering second particles with the saturated fluidized bed while allowing the liquid and at least some of first particles to flow out of the fluid chamber.

In a further aspect, the invention includes a method of separating components of a fluid. The method includes introducing into a vessel a priming fluid, the vessel defining a flow passage having a trap dam and a barrier, rotating the vessel about an axis of rotation to trap a portion of the priming fluid upstream the trap dam, passing into the vessel a fluid to be separated, allowing the components of the fluid to separate in the vessel according to density differences, accumulating at least a relatively intermediate density component of the fluid upstream the barrier while allowing relatively higher and lower density components of the fluid to flow past the barrier, guiding, with the trapped priming fluid, flow of the intermediate density component toward the barrier, and removing the accumulated intermediate density component from the vessel.

In an important aspect, the separated fluid is blood and the particles and/or components of the separated fluid are particles and/or components of blood. In addition, the priming fluid is blood.

In an additional aspect, the invention includes the combination of a single stage separation vessel and the fluid chamber.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
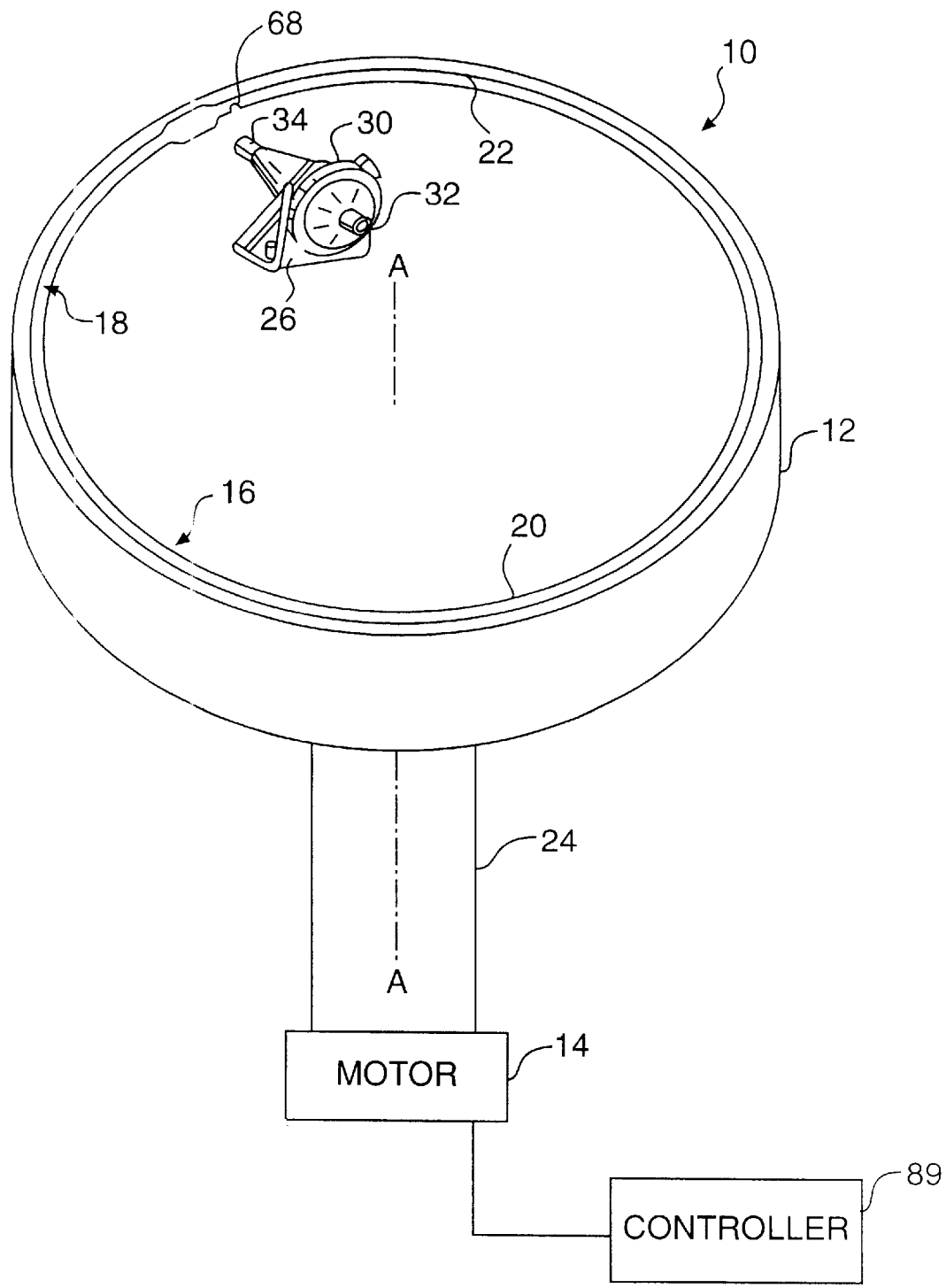
FIG. 1 is a partial perspective view of a centrifuge apparatus including a fluid chamber in accordance with an embodiment of the invention.

Reference will now be made in detail to the present preferred embodiments of the invention illustrated in the accompanying drawings. Wherever possible, the same reference numbers are used in the drawings and the description to refer to the same or like parts, and the same reference numerals with alphabetical suffixes are used to refer to similar parts.

The embodiments of the present invention preferably include a COBE® SPECTRA™ single stage blood component centrifuge manufactured by Cobe Laboratories of Colorado. The COBE® SPECTRA™ centrifuge incorporates a one-omega/two-omega sealless tubing connection as disclosed in U.S. Pat. No. 4,425,112 to Ito, the entire disclosure of which is incorporated herein by reference. The COBE® SPECTRA™ centrifuge also uses a single-stage blood component separation channel substantially as disclosed in U.S. Pat. No. 4,094,461 to Kellogg et al. and U.S. Pat. No. 4,647,279 to Mulzet et al., the entire disclosures of which are also incorporated herein by reference. The embodiments of the invention are described in combination with the COBE® SPECTRA™ centrifuge for case of discussion only, and is not intended to limit the invention in any sense.

As will be apparent to one having skill in the art, the present invention may be advantageously used in a variety of centrifuge devices commonly used to separate blood into its components. In particular, the present invention may be used with any centrifugal apparatus that employs a component collect line such as a platelet collect line or a platelet rich plasma line, whether or not the apparatus employs a single stage channel or a one-omega/two-omega sealless tubing connection.

As embodied herein and illustrated in FIG. 1, the present invention includes a centrifuge apparatus 10 having a centrifuge rotor 12 coupled to a motor 14 so that the centrifuge rotor 12 rotates about its axis of rotation A—A. The rotor 12 has a retainer 16 including a passageway or annular groove 18 having an open upper surface adapted to receive a separation vessel 28, 28a, or 28b shown respectively in FIGS. 2,3, and 5. The groove 18 completely surrounds the rotor's axis of rotation A—A and is bounded by an inner wall 20 and an outer wall 22 spaced apart from one another to define the groove 18 therebetween. Although the groove 18 shown in FIG. 1 completely surrounds the axis of rotation A—A, the groove only partially surrounds the axis A—A when the separation vessel is not generally annular. As compared to previous designs of the COBE® SPECTRA™ blood component centrifuge, the outer wall 22 is preferably spaced closer to the axis of rotation A—A to reduce the volume of the separation vessel 28, 28a, 28b and to increase flow velocity in the vessel 28, 28a, 28b.

Preferably, a substantial portion of the groove 18 has a constant radius of curvature about the axis of rotation A—A is and positioned at a maximum possible radial distance on the rotor 12. As described below, this shape ensures that substances separated in the separation vessel 28, 28a, 28b undergo relatively constant centrifugal forces as they pass from an inlet portion to an outlet portion of the separation vessel 28, 28a, 28b.

The motor 14 is coupled to the rotor 12 directly or indirectly through a shaft 24 connected to the rotor 12. Alternately, the shaft 24 may be coupled to the motor 14 through a gearing transmission (not shown).

As shown in FIG. 1, a holder 26 is provided on a top surface of the rotor 12. The holder 26 releasably holds a fluid chamber 30 on the rotor 12 so that an outlet 32 of the fluid chamber 30 is positioned closer to the axis of rotation A—A than an inlet 34 of the fluid chamber 30. The holder 26 preferably orients the fluid chamber 30 on the rotor 12 with a longitudinal axis of the fluid chamber 30 in a plane transverse to the rotor's axis of rotation A—A. Alternatively, the holder 26 may be arranged to hold the fluid chamber 30 on the rotor 12 with the fluid chamber outlet 32 facing the axis of rotation A—A. Although the holder 26 retains the fluid chamber 30 on a top surface of the rotor 12, the fluid chamber 30 may also be secured to the rotor 12 at alternate locations, such as beneath the top surface of the rotor 12.

Figure 2:
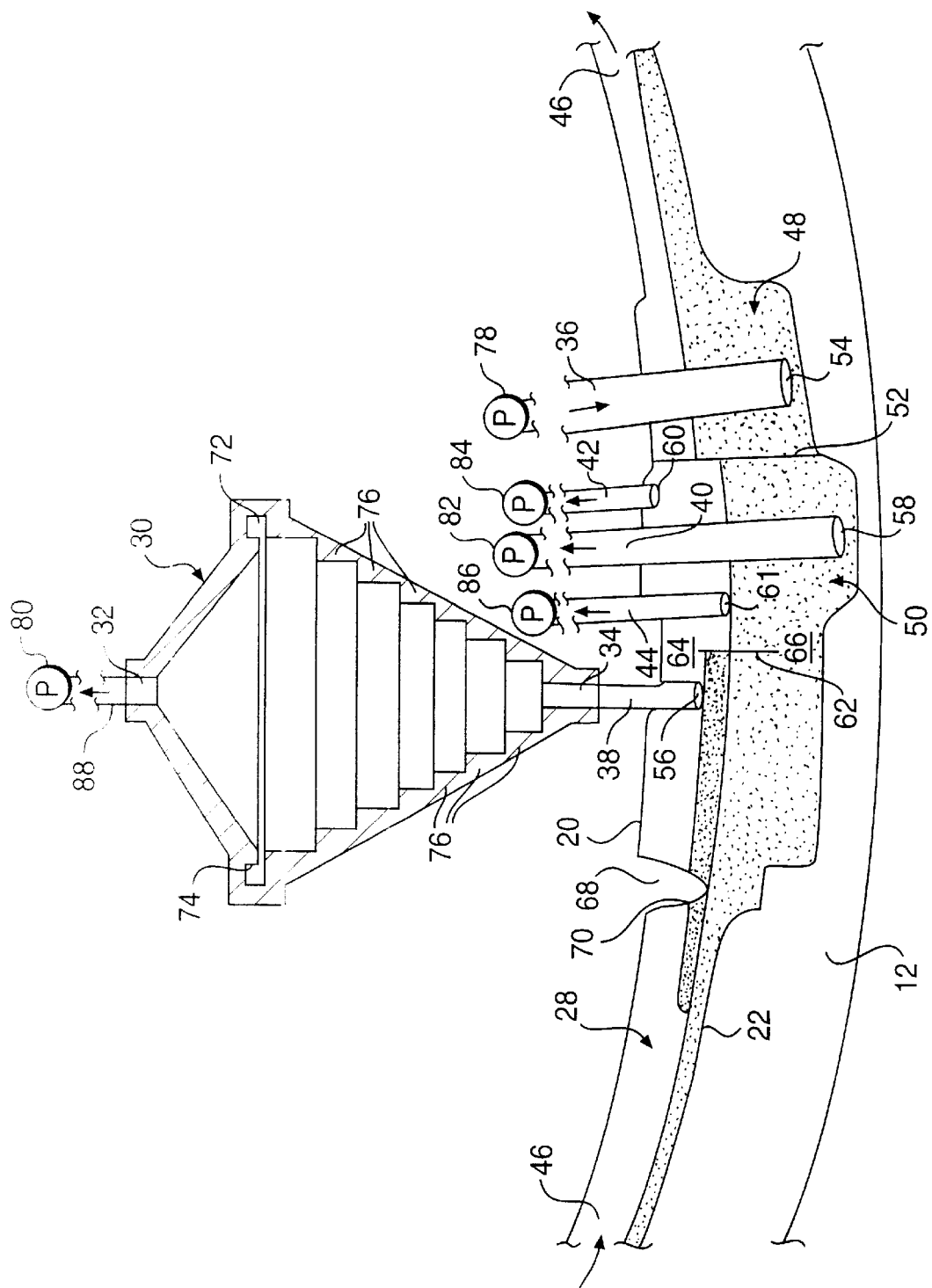
FIG. 2 is a partial cross-sectional view of a portion of a separation vessel and the fluid chamber mounted on the rotor of FIG. 1 during a separation procedure.

FIG. 2 schematically illustrates a portion of the separation vessel 28 and fluid chamber 30 mounted on the rotor 12. FIG. 2 also illustrates an inflow tube 36 for conveying a fluid to be separated, such as whole blood, into the separation vessel 28; first, second, and third collection lines 38, 40, 42 for removing separated substances from the separation vessel 28; and an interface control line 44 for adjusting the level of an interface between separated substances in the vessel 28. Preferably, the separation vessel 28 forms what is known as a single stage component separation area rather than forming a plurality of such stages. In other words, each of the components separated in the vessel 28 are collected and removed in only one area of the vessel 28. In addition, the separation vessel 28 includes a substantially constant radius except in the outlet portion 50 where the outer wall of the outlet portion is preferably positioned further away from the axis of rotation A—A to allow for the ports 56, 58, 60, and 61 to be positioned at different radial distances and to create a collection pool with greater depth for the high density red blood cells.

Although the ports 56a, 58a, and 60a and lines 38a, 40a, and 42a are referred to as being "collection" ports and lines, the substances removed through these ports and lines can be either collected or reinforced back into a donor.

The separation vessel 28 has a generally annular flow path 46 and includes an inlet portion 48 and outlet portion 50. A wall 52 prevents substances from passing directly between the inlet and outlet portions 48 and 50 without first flowing around the generally annular flow path 46 (e.g., counter-clockwise as illustrated by arrows in FIG. 2).

Although FIG. 2 shows the inlet portion 48 as having a wide radial cross-section, the outer wall of the inlet portion 48 can be spaced closer to the inner wall of the inlet portion 48 and/or tapered. An inlet port 54 of inflow tube 36 allows for flow of a substance to be separated, such as whole blood, into the inlet portion 48 of separation vessel 28. During a separation procedure, substances entering the inlet portion 48 follow the flow path 46 and stratify according to differences in density in response to rotation of the rotor 12. Preferably, the flow path 46 between the inlet and outlet portions 48 and 50 is curved and has a substantially constant radius. In addition, the flow path 46 is placed at the maximum distance from the axis A—A. This shape ensures that components passing through the flow path 46 encounter a relatively constant gravitational field and a maximum possible gravitational field for the rotor 12.

The separated substances flow into the outlet portion 50 where they are removed via first, second, and third collection ports 56, 58, and 60 respectively, of first, second, and third collection lines 38, 40, and 42. Separated substances are also removed by an interface control port 61 of the interface control line 44. As shown in FIG. 2, the first, second, and third ports 56, 58, and 60 are positioned at varying radial locations on the rotor 12 to remove substances having varying densities. The second collection port 58 is farther from the axis of rotation A—A than the first and third ports 56 and 60 to remove the most dense substances separated in the separation vessel 28, such as red blood cells. The third port 60 is located closer to the axis of rotation A—A than the first and second ports 56 and 58 to remove the least dense substances separated in the separation vessel 28, such as plasma.

The outlet portion 50 includes a barrier 62 for substantially blocking flow of intermediate density substances, such as platelets and some white blood cells. Preferably, the barrier 62 extends completely across the outlet portion 50 in a direction generally parallel to the axis of rotation A—A. The first collection port 56 is positioned immediately upstream of barrier 62, downstream of the inlet portion 48, to collect the intermediate density substances blocked by the barrier 62.

Radially inner and outer edges of the barrier 62 are spaced from radially inner and outer walls of the separation vessel 28 to form a first passage 64 for lower density substances, such as plasma, at a radially inner position in the outlet portion 50 and a second passage 66 for higher density substances, such as red blood cells, at a radially outer position in the outlet portion 50. The second and third collection ports 58 and 60 are positioned downstream of the barrier 62 to collect the respective lower and high density substances passing through the first and second passages 64 and 66.

The interface port 61 is also positioned downstream of the barrier 62. During a separation procedure, the interface port 61 removes the most dense or the least dense substances in the outlet portion 50 to thereby control the radial position of the interface between the intermediate density substances and other substances in the outlet portion 50. Alternatively, the second collection line 40 may be flow connected to the interface control line 44 so that substances flowing through the second collection line 40 and interface control line 44 are combined and removed together through a portion of the interface control line 44. Although the second and third collection ports 58 and 60 and the interface control port 61 are shown downstream of the barrier 62, one or more of these elements may be upstream of the barrier 62. In addition, the order of the collection ports 56, 58, 60, and the control port 61 along the length of the outlet portion 50 could be changed. Further details concerning the structure and operation of the separation vessel 28 are described in U.S. Pat. No. 4,094,461 to Kellogg et al. and U.S. Pat. No. 4,647,279 to Mulzet et al., which have been incorporated herein by reference.

As shown in FIGS. 1 and 2, a ridge 68 extends from the inner wall 20 of the groove 18 toward the outer wall 22 of the groove 18. When the separation vessel 28 is loaded in the groove 18, the ridge 68 deforms semi-rigid or flexible material in the outlet portion 50 of the separation vessel 28 to form a trap dam 70 on the radially inner wall of the separation vessel 28, upstream the first collection port 56. The trap dam 70 extends away from the axis of rotation A—A to trap a portion of lower density substances, such as priming fluid and/or plasma, along a radially inner portion of the separation vessel 28 located upstream the trap dam 70.

When the separation vessel 28 is used to separate whole blood into blood components, the trap dam 70 traps priming fluid and/or plasma and these trapped substances form a very thin and rapidly advancing red blood cell bed in the separation vessel 28. This reduces the amount of whole blood required to initiate a separation procedure. The trapped substances also help convey platelets to the outlet portion 50 and first collection port 56 by increasing plasma flow velocities next to the layer of red blood cells in the separation vessel 28 to scrub platelets toward the outlet portion 50.

Although the ridge 68 preferably deforms the separation vessel 28 to form the trap dam 70, the trap dam 70 could be formed in other ways. For example, the trap dam 70 could be a permanent structure extending from a radially inner wall of the separation vessel 28. In addition, the trap dam 70 could be positioned closer to the barrier 62 and have a small hole passing therethrough to allow for passage of air in a radial inner area of the outlet portion 50.

As shown in FIG. 2, the first collection line 38 is connected between the first collection port 56 and the fluid chamber inlet 34 to pass the intermediate density substances into the fluid chamber 30. Preferably, the fluid chamber 30 is positioned as close as possible to the first collection port 56 so that any red blood cells entering the fluid chamber 30 will be placed in a high gravitational field and compacted. As described below, particles and/or components initially separated in the separation vessel 28 are further separated in the fluid chamber 30. This further separation takes place by forming an elutriative field in the fluid chamber 30 or by forming a saturated fluidized bed of particles, such as platelets, in the fluid chamber 30.

The fluid chamber 30 is preferably constructed similar or identical to one of the fluid chambers disclosed in above-mentioned U.S. patent application Ser. Nos. 08/423,578 and 08/423,583. As shown in FIG. 2, the inlet 34 and outlet 32 of the fluid chamber 30 are arranged along a longitudinal axis of the fluid chamber 30. A wall of the fluid chamber 30 extends between the inlet 34 and outlet 32 thereby defining inlet 34, the outlet 32, and an interior of the fluid chamber 30.

The fluid chamber 30 includes two frustoconical shaped sections joined together at a maximum cross sectional area of the fluid chamber 30. The interior of the fluid chamber 30 tapers (decreases in cross-section) from the maximum cross-sectional area in opposite directions toward the inlet 34 and the outlet 32. Although the fluid chamber 30 is depicted with two sections having frustoconical interior shapes, the interior of each section may be paraboloidal, or of any other shape having a major cross-sectional area greater than the inlet or outlet area.

The volume of the fluid chamber 30 should be at least large enough to accommodate the formation of a saturated fluidized particle bed (described below) for a particular range of flow rates, particle sizes, and rotational speeds of the centrifuge rotor 12. The fluid chamber 30 may be constructed from a unitary piece of plastic or from separate pieces joined together to form separate sections of the fluid chamber 30. The fluid chamber 30 may be formed of a transparent or translucent copolyester plastic, such as PETG, to allow viewing of the contents within the chamber interior with the aid of an optional strobe (not shown) during a separation procedure.

As shown in FIG. 2, a groove 72 is formed on an inner surface of the fluid chamber 30 at a position of the maximum cross-sectional area. The groove 72 is defined by top and bottom wall surfaces oriented substantially perpendicular to the longitudinal axis of the fluid chamber 30 and an inner surface of the fluid chamber 30 facing the longitudinal axis. Preferably, the groove 72 is annular, however, the groove 72 may also partially surround the longitudinal axis of the fluid chamber 30.

The groove 72 helps to disperse Coriolis jetting within the fluid chamber 30, as described below. Sudden increases in liquid flow rate during a particle separation procedure may limit the ability of the saturated fluidized particle bed to obstruct particle passage. Liquid flowing into the fluid chamber 30 undergoes a Coriolis jetting effect. This jetting flow reduces the filtration effectiveness of the saturated fluidized particle bed because liquid and particles may pass between the saturated fluidized particle bed and an interior wall surface of the fluid chamber 30 rather than into the bed itself. The fluid chamber 30 including groove 72 counteracts these effects by channeling Coriolis jetting flow in a circumferential direction partially around the axis of fluid chamber 30. Therefore, the groove 72 improves the particle obstruction capability of the saturated bed, especially when liquid flow rates increase.

As shown in FIG. 2, a circumferential lip 74 extends from a top portion of the groove 72 toward a bottom portion of the groove 72 to define an entrance into the groove 72. The lip 74 functions to guide fluid in the groove 72.

A plurality of steps 76 are preferably formed on an inner surface of the fluid chamber 30 between the maximum cross-section of the chamber 30 and the inlet 34. Although six steps 76 are illustrated, any number of steps may be provided in the fluid chamber 30.

Each step 76 has a base surface oriented substantially perpendicular to the longitudinal axis of the fluid chamber 30, as well as a side surface positioned orthogonal to the base surface. Although FIG. 2 depicts a corner where the side surface and the base surface intersect, a concave groove may replace this corner. In a preferred embodiment, each step 76 is annular and surrounds the axis of the chamber 30 completely to bound a cylindrical shaped area. Alternatively, the steps 76 may partially surround the axis of the chamber 30.

Adding steps 76 to the fluid chamber 30, also improves the particle obstruction characteristics of a saturated fluidized particle bed formed in the fluid chamber 30, in particular during increases in the rate of fluid flow. The steps 76 provide this improvement by providing momentum deflecting and redirecting surfaces to reduce Coriolis jetting in fluid chamber 30. When Coriolis jetting takes place, the liquid and particles of the jet travel along an interior surface of the fluid chamber 30 that faces the direction of centrifuge rotation. Therefore, the jet may transport particles between the fluid chamber interior surface and either a saturated fluidized particle bed or an elutriation field positioned in the fluid chamber 30. Thus, particles traveling in the jet may exit the fluid chamber 36 without being separated.

Steps 76 direct or alter the momentum of the Coriolis jet flow of liquid and particles generally in a circumferential direction about the axis of the fluid chamber 30. Thus, a substantial number of particles originally flowing in the jet must enter the saturated fluidized bed or elutriation field to be separated.

The groove 72 and steps 76 are provided to facilitate fluid flow rate increases, as well as to improve steady state performance of the fluid chamber 30. During blood component separation, the groove 72 and steps 76 greatly reduce the number of white blood cells that would otherwise bypass a saturated fluidized platelet bed formed in the fluid chamber 30.

As schematically shown in FIG. 2, a plurality of pumps 78, 80, 82, 84, 86 are provided for adding and removing substances to and from the separation vessel 28 and fluid chamber 30. An inflow pump 78 is coupled to the inflow line 36 to supply a substance to be separated, such as whole blood, to the inlet portion 48. A first collection pump 80 is coupled to outflow tubing 88 connected to the fluid chamber outlet 32. The first collection pump 80 draws fluid and particles from the fluid chamber outlet 32 and causes fluid and particles to enter the fluid chamber 30 via the fluid chamber inlet 34.

Second and third collection pumps 82 and 84 are coupled respectively to the second and third collection lines 40 and 42 for removing substances through the second and third collection ports 58 and 60. Similarly, interface control pump 86 is coupled to interface control line 44 to remove substances via the interface control port 61. Preferably, the second collection line 40 and interface control line 44 are flow connected together and only one of the second collection pump 82 and interface control pump 86 is provided. In other words, only four of the five pumps 78, 80, 82, 84, and 86 are preferably provided.

The pumps 78–86 are preferably peristaltic pumps or impeller pumps configured to prevent significant damage to blood components. However, any fluid pumping or drawing device may be provided. In an alternative embodiment (not shown), the first collection pump 80 may be fluidly connected to the fluid chamber inlet 34 to directly move substances into and through the fluid chamber 30. The pumps 78–86 may be mounted at any convenient location.

As shown in FIG. 1, the apparatus 10 further includes a controller 89 connected to the motor 14 to control rotational speed of the rotor 12. In addition, the controller 89 is also preferably connected to the pumps 78–86 to control the flow rate of substances flowing to and from the separation vessel 28 and the fluid chamber 30. The controller 89 maintains a saturated fluidized bed of first particles within the fluid chamber 30 to cause second particles to be retained in the fluid chamber 30. The controller 89 may include a computer having programmed instructions provided by a ROM or RAM as is commonly known in the art.

The controller 89 may vary the rotational speed of the centrifuge rotor 12 by regulating frequency, current, or voltage of the electricity applied to the motor 14. Alternatively, the rotational speed can be varied by shifting the arrangement of a transmission (not shown), such as by changing gearing to alter a rotational coupling between the motor 14 and rotor 12. The controller 89 may receive input from a rotational speed detector (not shown) to constantly monitor the rotation speed of the rotor 12.

The controller 89 may also regulate one or more of the pumps 78–86 to vary the flow rates for substances supplied to or removed from the separation vessel 28 and the fluid chamber 30. For example, the controller 89 may vary the electricity provided to the pumps 78–86. Alternatively the controller 89 may vary the flow rate to and from the vessel 28 and the fluid chamber 30 by regulating valving structures (not shown) positioned in the lines 36, 38, 40, 42 and/or 89. The controller 89 may receive input from a flow detector (not shown) positioned within the first collection line 38 to monitor the flow rate of substances entering the fluid chamber 30. Although a single controller 89 having multiple operations is schematically depicted in the embodiment shown in FIG. 1, the controlling structure of the invention may include any number of individual controllers, each for performing a single function or a number of functions. The controller 89 may control flow rates in many other ways as is known in the art.

Figure 3:
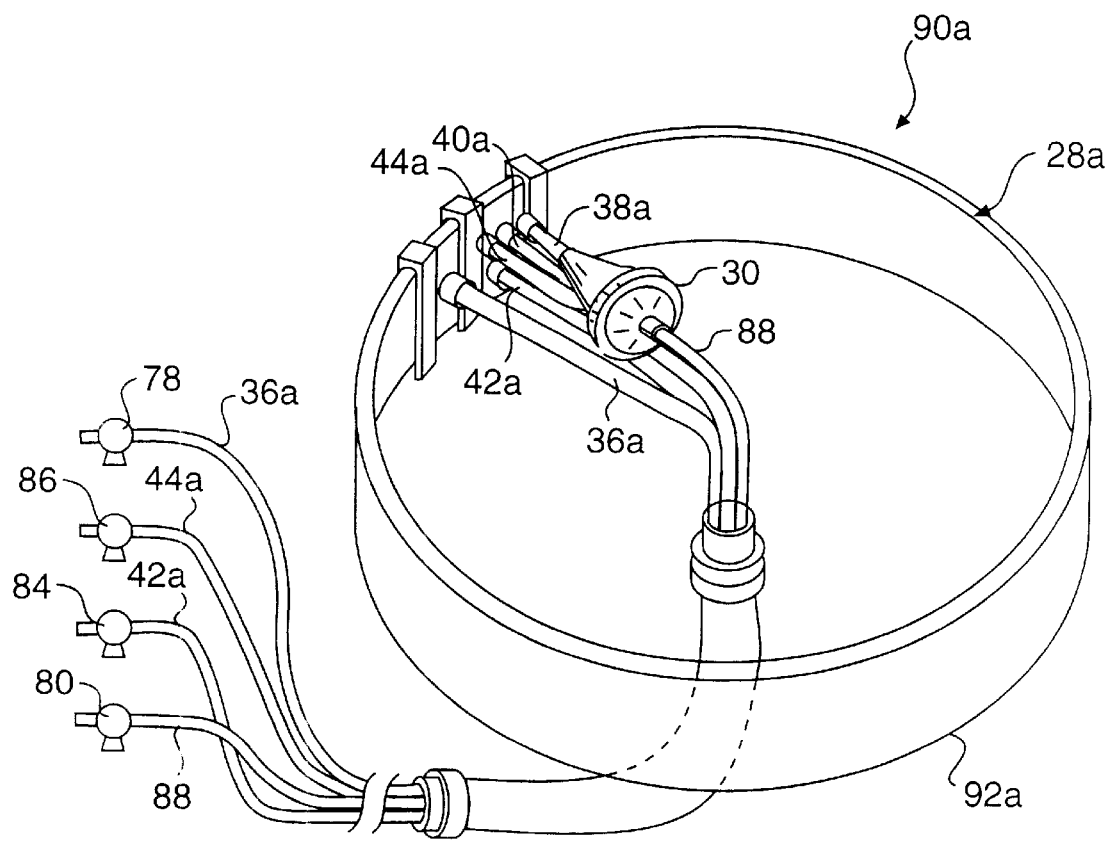
FIG. 3 is a perspective view of a first embodiment of the separation vessel and fluid chamber for use in the apparatus of FIG. 1.
Figure 4:
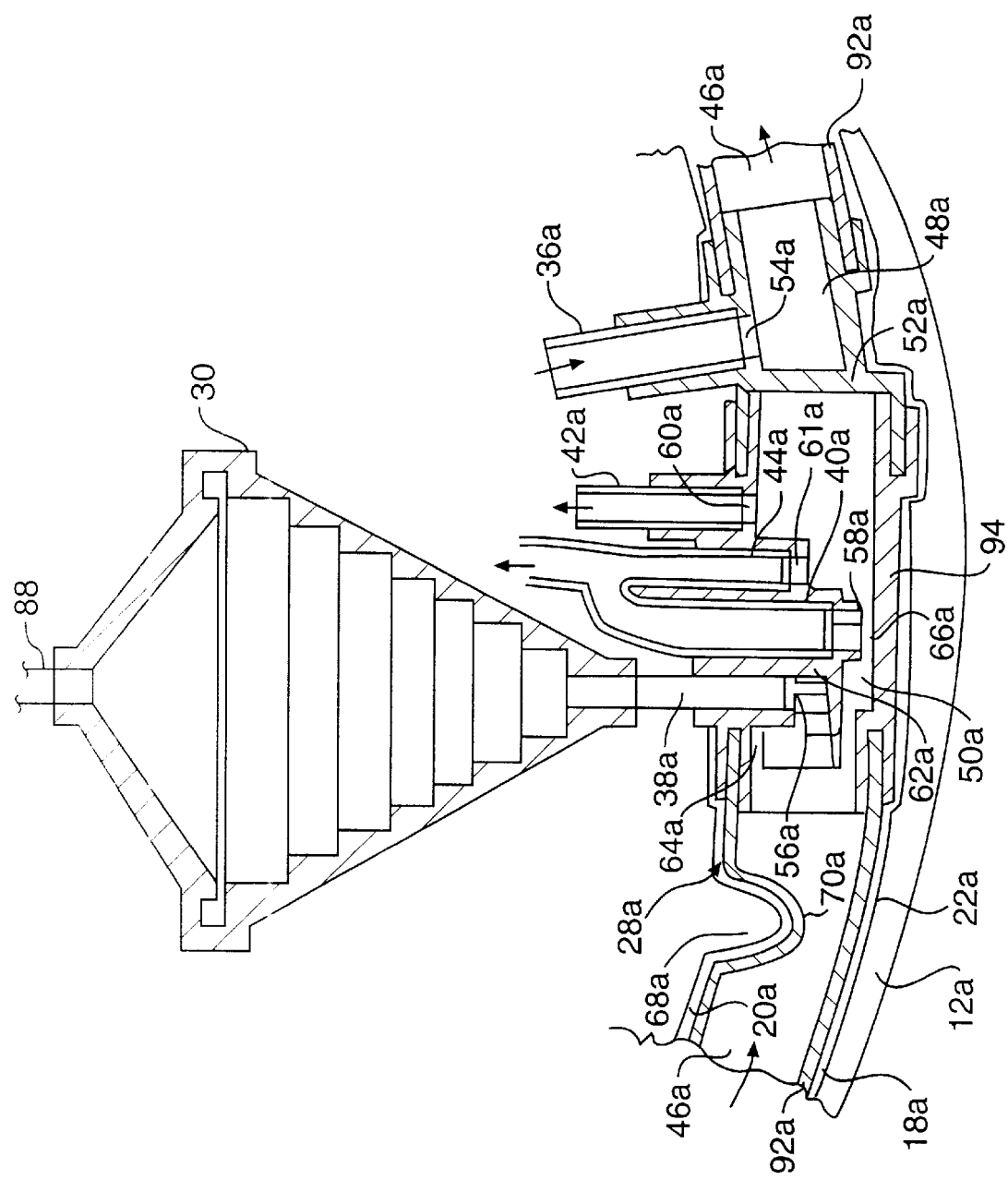
FIG. 4 is a partial cross sectional view of inlet and outlet portions of the separation vessel and the fluid chamber of FIG. 3 on a rotor.

FIG. 3 shows an embodiment of a tubing set 90a for use in the apparatus 10, and FIG. 4 illustrates a cross-sectional view of a portion of the tubing set 90a mounted in groove 18a on rotor 12a. The tubing set 90a includes a separation vessel 28a, the fluid chamber 30, an inflow tube 36a for conveying a fluid to be separated, such as whole blood, into the separation vessel 28a, first, second, and third collection lines 38a, 40a, 42a for removing separated substances from the separation vessel 28a, and an interface control line 44a for adjusting the level of an interface between separated substances in the vessel 28a. When the separation vessel 28a is mounted on the rotor 12a the lines 36a, 42a, 44a, and 48 preferably pass through slots (not shown) formed on the rotor 12a.

Preferably, the separation vessel 28a is constructed like the centrifugal separator disclosed in above-mentioned U.S. Pat. No. 4,647,279 to Mulzet et al. The separation vessel 28a includes a generally annular channel 92a formed of semi-rigid or flexible material and having a flow path 46a (FIG. 4). As shown in FIG. 4, opposite ends of the channel 92a are connected to a relatively rigid connecting structure 94 including an inlet portion 48a and outlet portion 50a for the separation vessel 28a separated by a wall 52a. An inlet port 54a of inflow tubing 36a is in fluid communication with the inlet portion 48a and allows for flow of a substance to be separated, such as blood, into the separation vessel 28a. During a separation procedure, substances entering the vessel 28a via the inlet port 54a flow around the channel 92a (counterclockwise in FIG. 4) via the flow path 46a and stratify according to differences in density in response to rotation of the rotor 12a.

The separated substances flow into the outlet portion 50a where they are removed through first, second and third collection ports 56a, 58a, 60a of respective first, second, and third collection lines 38a, 40a, and 42a and an interface control port 61a the interface control line 44a. As shown in FIG. 4, the first, second, and third ports 56a, 58a, and 60a are positioned at varying radial locations on the rotor 12a to remove substances having different densities. The second collection port 58a is farther from the axis of rotation A—A than the first and third collection ports 56a and 60a to remove the most dense substances separated in the separation vessel 28a, such as red blood cells. The third port 60a is located closer to the axis of rotation A—A than the first and second ports 56a and 58a to remove the least dense substances separated in the separation vessel 28a, such as plasma.

The outlet portion 50a includes a barrier 62a for substantially blocking flow of intermediate density substances, such as platelets and some white blood cells. In the embodiment shown in FIG. 4, the barrier 62a is a skimmer dam extending across the inlet portion in a direction generally parallel to the axis of rotation A—A. The first collection port 56a is positioned immediately upstream of the skimmer dam 62a, downstream of the inlet portion 48a, to collect the intermediate density substances blocked by the skimmer dam 62a.

Radially inner and outer edges of the skimmer dam 62a are spaced from radially inner and outer walls of the separation vessel 28a to form a first passage 64a for lower density substances, such as plasma, at a radially inner position in the outlet portion 50a and a second passage 66a for higher density substances, such as red blood cells, at a radially outer position in the outlet portion 50a. The second and third collection ports 58a and 60a are positioned downstream the skimmer dam 62a to collect the respective lower and higher density substances passing through the first and second passages 64a and 66a.

The interface port 61a is positioned at approximately the same radial distance as the first collection port 56a. During a separation procedure, the interface port 61a removes either the most dense or the least dense separated substances in the outlet portion 50a to control the radial position of the interface between the intermediate density substances and other substances in the outlet portion 50a. As shown in FIGS. 3 and 4, the second collection line 40a is preferably connected to the interface control line 44a so that substances flowing through the second collection line 40a and interface control line 44a are removed together through a portion of the interface control line 44a.

As shown in FIG. 4, a ridge 68a extends from the inner wall 20a of the groove 18a toward the outer wall 22a of the groove 18a. When the separation vessel 28a is loaded in the groove 18a, the ridge 68a deforms the semi-rigid or flexible material of the separation vessel 28a to form a trap dam 70a on the radially inner wall of the separation vessel 28a between the first collection port 56a and the inlet portion of the separation vessel 48a. The trap dam 70a extends away from the axis of rotation A—A to trap a portion of lower density substances, such as priming fluid and/or plasma, along a radially inner portion of the separation vessel 28a. The trap dam 70a functions like the trap dam 70 of FIG. 2 and could be permanent structure formed in the vessel 28a.

Figure 5:
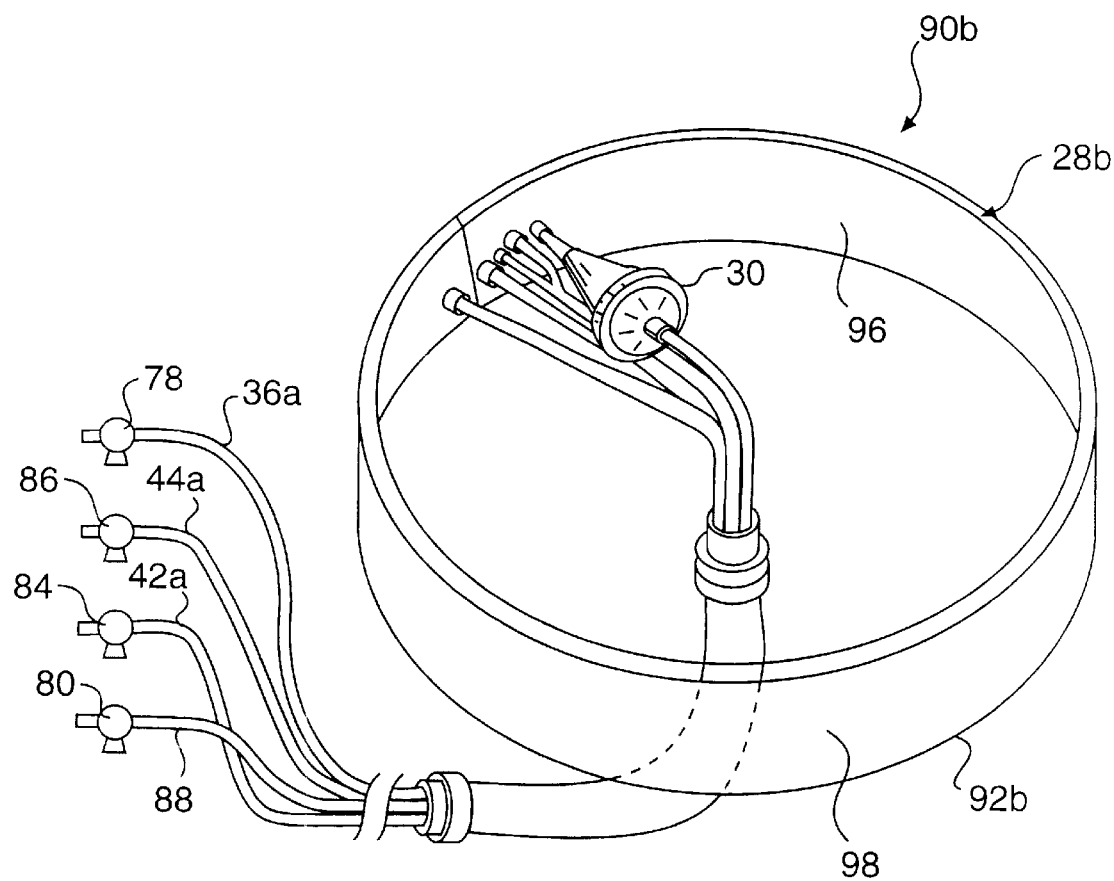
FIG. 5 is a perspective view of a second embodiment of the separation vessel and fluid chamber for use in the apparatus of FIG. 1.

FIG. 5 shows a second embodiment of a tubing set 90b for use in the apparatus 10. The tubing set 90b includes a separation vessel 28b having a generally annular channel 92b including an inlet portion and outlet portion formed directly in the channel 92b itself rather than in a separate connecting structure. In a preferred embodiment, the channel 92b includes an inner wall 96 and an outer wall 98 sealed together by heat sealing, for example, at top and bottom edges to form a flow passage therebetween. It is understood that the channel 92b can also be construed of a single extruded piece or from a single sheet sealed together by heat sealing, for example, along a single edge. Preferably, the inner wall 96 and the outer wall 98 are both entirely formed of semi-rigid or flexible plastic material so that the channel can be deformed by the trap ridge 68 in groove 18. Alternatively, the inner and outer walls 96 and 98 may include flexible or semi-rigid material only in the outlet portion.

Figure 6:
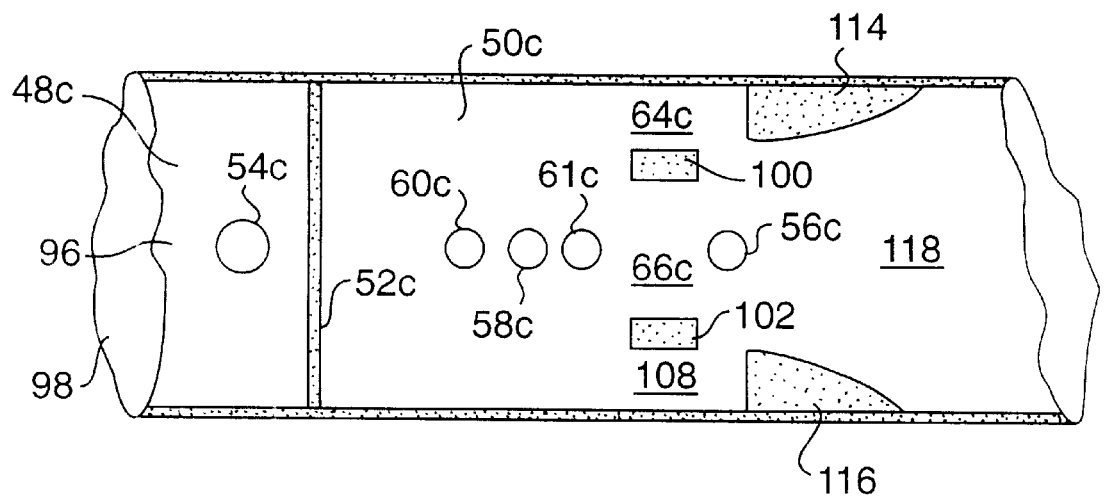
FIG. 6 illustrates inlet portions and outlet portions of a first alternate embodiment of the separation vessel of FIG. 5.

FIG. 6 shows an embodiment of an inlet portion 48c and outlet portion 50c for the tubing set 90b of FIG. 5. A first sealed portion 52c extending from top edges of the inner and outer walls 96 and 98 to bottom edges of the inner and outer walls 96 and 98 prevents fluid flow in a segment between the inner and outer walls 96 and 98 and defines the inlet and outlet portions 48c and 50c. Outlet ports 56c, 58c, and 60c and an interface control port 61c are formed in the outlet portion 50c. An inlet port 54c is formed in the inlet portion 48c. As shown in FIG. 6, second and third sealed portions 100 and 102 are spaced from top and bottom edges of the inner and outer walls 96 and 98 and from each other. The second and third sealed portions 100 and 102 prevent fluid flow in sealed portions 100 and 102 to form a first passage 64c between a top of the outlet portion 50c and the second sealed portion 100, a second passage 66c between the second and third sealed portions 100 and 102, and a third passage 108 between the second sealed portion 100 and the bottom of the outlet portion 50c.

Figure 7:
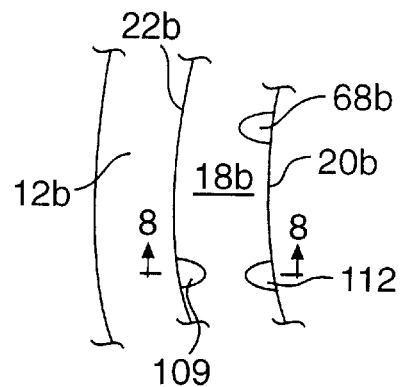
FIG. 7 is a top view of a portion of a centrifuge rotor in an embodiment of the invention for use with separation vessels of FIGS. 6 and 9.
Figure 8A:
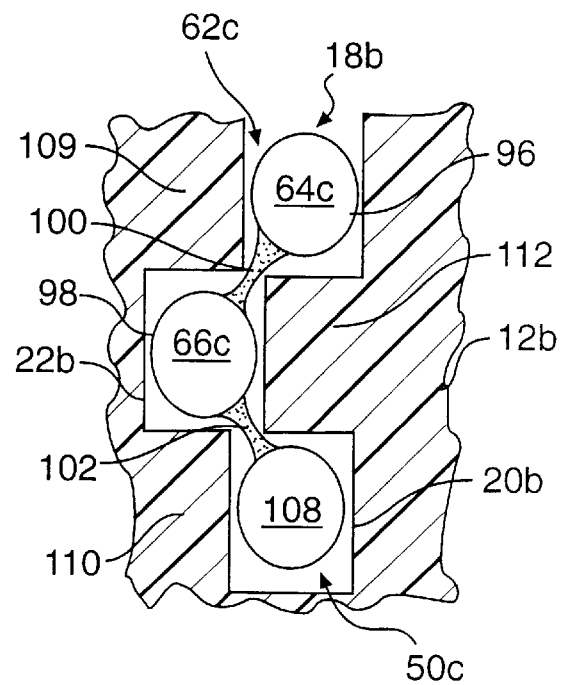
FIG. 8a is a cross-sectional view taken along line 8—8 of FIG. 7 showing the separation vessel of FIG. 6 and an alternate embodiment of a retainer for the rotor of FIG. 1.

FIG. 7 shows a portion of a groove 18b on a centrifuge rotor 12b for use with the tubing set 90b shown in FIGS. 5 and 6. FIG. 8a shows a cross-sectional view of the outlet portion 50c when this tubing set 90b is mounted in the groove 18b. As illustrated in FIG. 7, first outer ridge 109 extends toward the inner wall 20b of the groove 18b from an upper portion of the outer wall 22b of the groove 18b. A second outer ridge 110 (hidden beneath ridge 109 in FIG. 7) extends toward the inner wall 20b of the groove 18b from a lower portion of the outer wall 22b of the groove 18b. An inner ridge 112 extends toward the outer wall 22b from a mid portion of the inner wall 20b so that the inner ridge 112 is spaced from and is between the first and second outer ridges 108 and 110. Alternatively, the groove 18b for the tubing set of FIGS. 5 and 6 may include a pair of inner wall ridges and a single outer wall ridge.

As shown in FIG. 8a, the first and second outer ridges 109 and 110 and the inner ridge 112 deform the outlet portion 50c to form a pair of dams on the outer wall 98, a dam on the inner wall 96, and a barrier 62c in the outlet portion 50c. As shown in this figure, the first and second outer ridges 109 and 110 and the inner ridge 112 cooperate to deform the outlet portion 50c and place the first and third passages 64c and 108 closer to the axis of rotation A—A than the second passage 66c. During a separation procedure, the barrier 62c substantially blocks passage of intermediate density substances in the outlet portion 50c, while lower density substances flow through the first and third passages 64c and 108 and higher density substances flow through the second passage 66c. These intermediate density substances are then removed from the outlet portion 50c via the first collection port 56c (FIG. 6) positioned in the separation vessel 28c between the inlet portion 48c and the second and third sealed portions 100 and 102.

Although FIGS. 7 and 8a show ends of the outer ridges 109 and 110 spaced from the end of the inner ridge 112 in the radial direction for purposes of illustration, these ends preferably overlap in the radial direction. In other words, an end portion of outer ridge 109 is directly above an end portion of inner ridge 112, and an end portion of inner ridge 112 is directly above an end portion of outer ridge 110.

As shown in FIG. 6, the outlet portion 50c preferably includes a fourth sealed portion 114 along the top of the outlet portion and a fifth sealed portion 116 along a bottom of the outlet portion 50c. The fourth and fifth sealed portions 114 and 116 are preferably located upstream of the first collection port 56c and downstream of the inlet portion 48c to define a restricted flow passage 118 therebetween. The restricted flow passage 118 guides substances in the outlet portion 50c toward the first collection port 56c and the barrier 62c and reduces the likelihood of low flow rate pockets forming in the outlet portion 50c.

The sealed portions 52c, 100, 102, 114, and 116 are preferable heat seals wherein the inner and outer walls 96 and 98 of the separation vessel 28b are welded to one another. Those skilled in the art will recognize that other types of seals or welds, such as adhesive bonds, could also be used. In addition, the sealed portions 52c, 100, 102, 114, and 116 could be formed by permanent structure placed between the first and second walls to block or alter flow.

Figure 9:
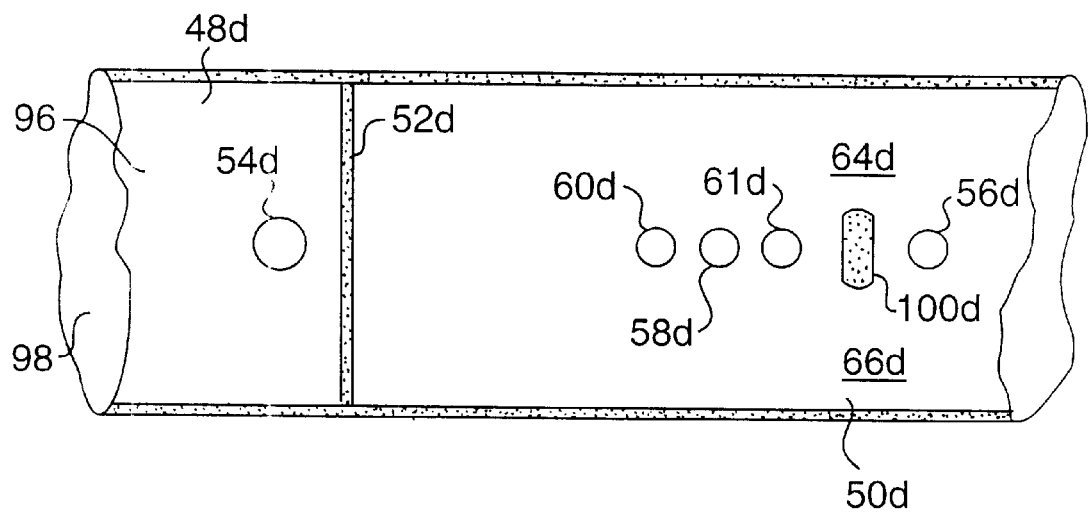
FIG. 9 is a view similar to FIG. 6 of a second alternate embodiment of the separation vessel of FIG. 5.

FIG. 9 shows an alternate embodiment of an inlet portion 48d and an outlet portion 50d for the separation vessel 28b of FIG. 5. As shown in this figure, the outlet portion 50d includes a second sealed portion 100d between the top and bottom of the outlet portion 50d. The top of the outlet portion 50d and the second sealed portion 100d define a first passage 64d in the outlet portion 50d, and the bottom of the outlet portion 50d and the second sealed portion 100d define a second passage 66d in the outlet portion 50d. Optionally, the outlet portion 50d also may include a restricted flow passage (not shown) similar to the restricted flow passage 118 shown in FIG. 6.

Figure 8B:
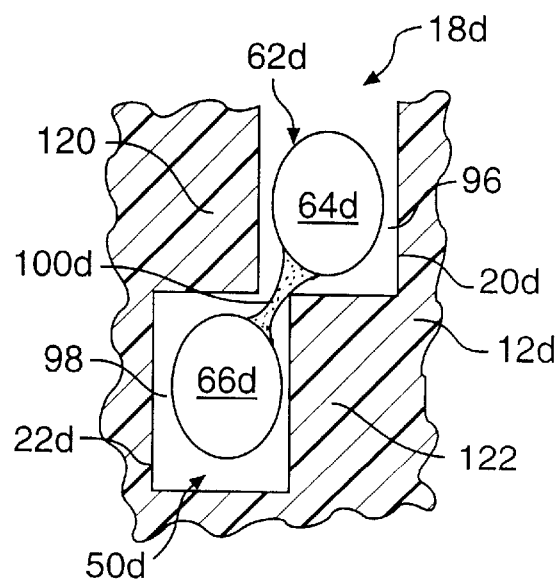
FIG. 8b is a cross-sectional view similar to FIG. 8a showing the separation vessel of FIG. 9 and another alternate embodiment of the retainer for the rotor of FIG. 1.

FIG. 8b shows a cross-sectional view of the outlet portion 50d when the tubing set of FIGS. 5 and 9 is mounted on a rotor 12d having a groove 18d. An outer ridge 120 extends toward the inner wall 20d of the groove 18d from an upper portion of the outer wall 22d of the groove 18d, and an inner ridge 122 extends toward the outer wall 22d of the groove 18d from a lower portion of the inner wall 20d of the groove 18d. Optionally, the groove for the tubing set of FIGS. 5 and 8b may include an outer ridge extending from a lower portion of the outer wall 22d and an inner ridge extending from an upper portion of the inner wall 20d.

As shown in FIG. 8b, the outer and inner ridges 120 and 122 deform the outlet portion 50d to form opposite facing dams and a barrier 62d in the outlet portion 50d. As shown in this figure, the outer and inner ridges 120 and 122 place the first passage 64d closer to the axis of rotation A—A than the second passage 66d. During a separation procedure, the barrier 62d substantially blocks passage of intermediate density substances in the outlet portion 50d, while lower density substances flow through the first passages 64d and higher density substances flow through the second passage 66d. These intermediate density substances are then removed from the outlet portion 50d via the first collection port 56d (FIG. 9) positioned in the separation vessel.

Although FIG. 8B shows the end of the outer ridge 120 spaced from the end of the inner ridge 122 for purposes of illustration, these ends preferably overlap in the radial direction. In other words, an/end portion of the outer ridge 120 is directly above an end portion of the inner edge 122.

Figure 10:
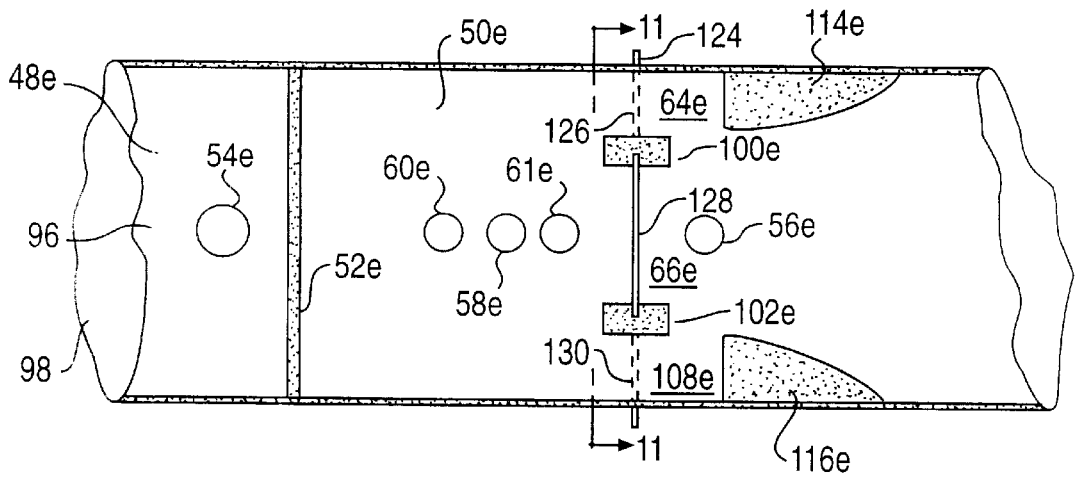
FIG. 10 is a view similar to FIG. 6 of a third alternate embodiment of the separation vessel of FIG. 5.

FIG. 10 shows another embodiment of an outlet portion 50e of the tubing set of FIG. 5 for use with a rotor lacking the inner and outer ridges 109, 110, 112, 120, and 122, shown in FIGS. 7, 8a, and 8b. The outlet portion 50e of FIG. 10 includes sealed portions 52e, 100e, 102e, 114e, and 116e similar to the sealed portions of FIG. 6. An elongate member 124, such as a dowel, extends through both the inner and outer walls 96 and 98 at the second and third seals 100e and 102e. A first portion of the elongate member 124 forms a first support 126 positioned along the outer wall 98 adjacent to first passage 64e. A second portion of the elongate member 124 forms a second support 128 positioned along the inner wall 96 adjacent to second passage 66e. A third portion of the elongate member 124 forms a third support 130 positioned along the outer wall 98 adjacent to third passage 108e.

Figure 11:
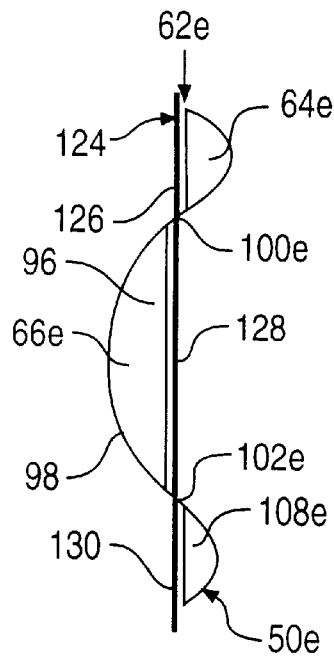
FIG. 11 is a cross-sectional view taken along line 11—11 of FIG. 10.

FIG. 11 is a cross-sectional view showing how the elongate member 124 cooperates with the sealed portions 100e and 102e to form a barrier 62e in the outlet portion 50e. The first and third supports 126 and 130 function like the first and second outer ridges 109 and 110 of FIG. 8a, and the second support 128 functions like the inner ridge 112 of FIG. 8a. When the tubing set of FIGS. 5, 10, and 11 is mounted on the rotor 12, the first and third supports 126 and 130 are positioned between the outer wall 22 of the groove 18 and the outer wall 98, and the second support 128 is positioned between the inner wall 96 and the inner wall 20 of the groove 18. This places the first and third passages 64e and 108e closer to the axis of rotation A—A than the second passage 66e and forms a pair of dams on the outer wall 98, a dam on the inner wall 96, and a barrier 62e in the outlet portion 50e.

Although the first support 126 and third support 130 are positioned on the outer wall 98 and the second support 128 is positioned on the inner wall 96, this configuration could be reversed to position the first support 126 and third support 130 on the outer wall 98 and to position the second support 128 on the inner wall 96.

Figure 12:
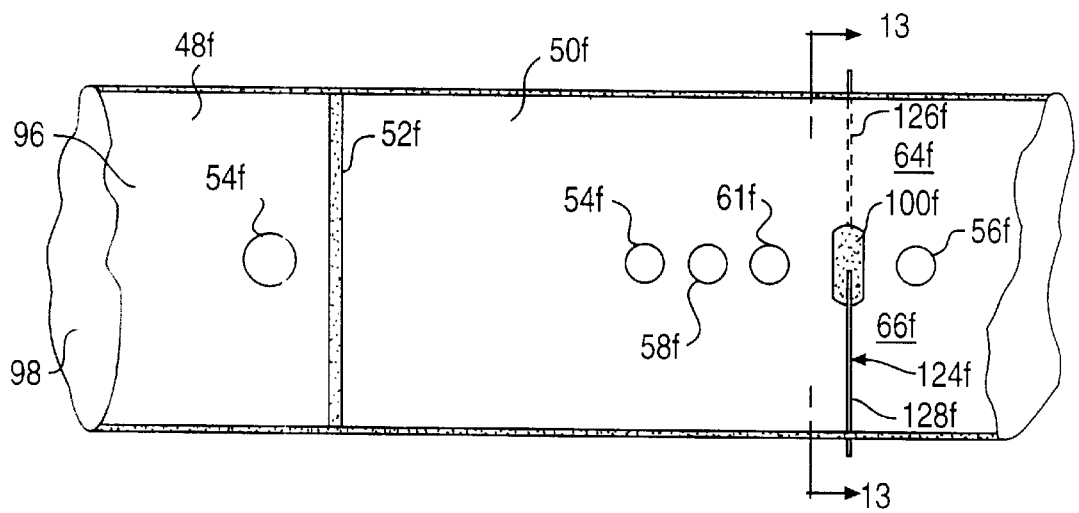
FIG. 12 is a view similar to FIG. 6 of a fourth alternate embodiment of the separation vessel of FIG. 5.

FIG. 12 shows another embodiment of an outlet portion 50f of the tubing set of FIG. 5 for use with a rotor lacking the inner and outer ridges 108, 110, 112, 120, and 122, shown in FIGS. 7, 8a, and 8b. The outlet portion 50f of FIG. 12 includes a sealed portion 100f similar to the sealed portion 100d of FIG. 9. An elongate member 124f, such as a dowel, extends through both the inner and outer walls 96 and 98 at the sealed portion 100f. A first portion of the elongate member 124f forms a first support 126f positioned along the outer wall 98 adjacent to first passage 64f, and a second portion of the elongate member 124f forms a second support 128f positioned along the inner wall 96 adjacent to second passage 66f.

Figure 13:
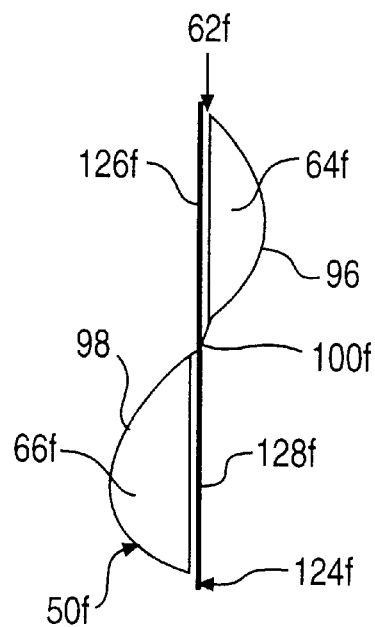
FIG. 13 is a cross-sectional view taken along line 13—13 of FIG. 12.

FIG. 13 is a cross-sectional view showing how the elongate member 124f cooperates with the sealed portion 100f to form a barrier 62f in the outlet portion 50f. The first support 126f functions like the outer ridge 120 of FIG. 8b and the second support 128f functions like the inner ridge 122 of FIG. 8b. When the tubing set of FIGS. 5, 12, and 13 is mounted on the rotor 12, the first support 126f is positioned between the outer wall 22 of the groove 18 and the outer wall 98 of portion 50f, and the second support 128f is positioned between the inner wall 96 and the inner wall 20 of the groove 18. This places first passage 64f closer to the axis of rotation A—A than second passage 66f and forms a pair of opposite facing dams and a barrier 62f in the outlet portion 50f.

Although the first support 126f is positioned on the outer wall 98 and the second support 128f is positioned on the inner wall 96, this configuration could be reversed to position the first support 126f on the outer wall 98 and to position the second support 128f on the inner wall 96.

For the embodiments shown in FIGS. 10–13, structure is preferably provided in the groove 18 or on the elongate member 124, 124f to orient the elongate member 124, 124 parallel to the axis of rotation A—A.

Methods of separating components or particles of blood are discussed below with reference to FIGS. 1 and 2. Although the invention is described in connection with blood component separation processes, it should be understood that the invention in its broadest sense is not so limited. The invention may be used to separate a number of different particles and/or fluid components. In addition the invention is applicable to both double needle and single needle blood purification or filtration applications. For example, the invention may be practiced with the SINGLE NEEDLE RECIRCULATION SYSTEM FOR HARVESTING BLOOD COMPONENTS of U.S. Pat. No. 5,437,624, the disclosure of which is incorporated herein by reference.

Preferably the separation vessel 28 and chamber 30 are initially primed with a low density fluid medium, such as air, saline solution, or plasma, having a density less than or equal to the density of liquid plasma. Alternatively, the priming fluid is whole blood itself. This priming fluid allows for efficient establishment of a saturated fluidized bed of platelets within the fluid chamber 30. When saline solution is used, the pump 78 (FIG. 2) pumps this priming fluid through the inflow line 36 and into the separation vessel 28 via the inlet port 54. The saline solution flows from the inlet portion 48 to the outlet portion 50 (counterclockwise in FIG. 2) and through the fluid chamber 30 when the controller 89 activates the pump 80. Controller 89 also initiates operation of the motor 14 to rotate the centrifuge rotor 12, separation vessel 28, and fluid chamber 30 about the axis of rotation A—A. During rotation, twisting of lines 36, 38, 40, 42, and 88 is prevented by a sealless one-omega/two-omega tubing connection as is known in the art and described in above-mentioned U.S. Pat. No. 4,425,112.

As the separation vessel 28 rotates a portion of the priming fluid (blood or saline solution) becomes trapped upstream the trap dam 70 and forms a dome of priming fluid (plasma or saline solution) along an inner wall of the separation vessel 28 upstream the trap dam 70. After the apparatus 10 is primed, and as the rotor 10 rotates, whole blood or blood components are introduced through the inlet port 54 into the separation vessel 28. When whole blood is used, the whole blood can be added to the separation vessel 28 by transferring the blood directly from a donor through inflow line 36. In the alternative, the blood may be transferred from a container, such as a blood bag, to inflow line 36.

The blood within the separation vessel is subjected to a centrifugal force causing components of the blood to separate. The components of whole blood stratify in order of decreasing density as follows: 1. red blood cells, 2. white blood cells, 3. platelets, and 4. plasma. The controller 89 regulates the rotational speed of the centrifuge rotor 12 to ensure that this particle stratification takes place. A layer of red blood cells forms along the outer wall of the separation vessel 28 and a layer of plasma forms along the inner wall of the separation vessel. Between these two layers, the intermediate density platelets and white blood cells form a buffy coat layer. This separation takes place while the components flow from the inlet portion 48 to the outlet portion 50. Preferably, the radius of the flow path 46 between the inlet and outlet portions 48 and 50 is substantially constant to maintain a steady red blood cell bed in the outlet portion even if flow changes occur.

In the outlet portion 50, platelet poor plasma and some white blood cells flow through the first passage 64 and downstream of the barrier 62 where they are removed via the third collection port 60. Red blood cells flow through the second passage 66 and downstream of the barrier 62 where they are removed via the second collection port 58. After the red blood cells, white blood cells, and plasma are thus removed, they are collected and recombined with other blood components or further separated. Alternately, these removed blood components may be reinfused into a donor.

A substantial portion of the platelets and some of the red blood cells accumulate upstream of the barrier 62. The accumulated platelets are removed via the first collection port 56 along with some of the white blood cells and plasma, and possibly some of the red blood cells. These components flow into the fluid chamber 30, filled with the priming fluid, so that a saturated fluidized particle bed may be formed. The portion or dome of priming fluid (i.e. saline) trapped along the inner wall of the separation vessel 28 upstream the trap dam 70 guides platelets so that they flow toward the barrier 62 and the first collection port 56. The trapped fluid reduces the effective passageway volume and area in the separation vessel 28 and thereby decreases the amount of blood initially required to prime the system in a separation process. The reduced volume and area also induces higher plasma and platelet velocities next to the stratified layer of red blood cells, in particular, to "scrub" platelets, toward the barrier 62 and first collection port 56. The rapid conveyance of platelets increases the efficiency of collection.

During a blood component separation procedure, the priming fluid trapped upstream the trap dam 70 may eventually be replaced by other fluids such as low density platelet poor plasma flowing in the separation vessel 28. Even when this replacement occurs, a dome or portion of trapped fluid is still maintained upstream the trap dam 70.

Accumulated platelets, white blood cells, and some plasma and red blood cells, are removed via the first collection port 56 and flow into the fluid chamber 30 so that the platelets form a saturated fluidized particle bed. The controller 89 maintains the rotation speed of the rotor 12 within a predetermined rotational speed range to facilitate formation of this saturated fluidized bed. In addition, the controller 89 regulates the pump 80 to convey at least the plasma, platelets, and white blood cells at a predetermined flow rate through the first collection line 38 and into inlet 34 of the fluid chamber 30. These flowing blood components displace the priming fluid from the fluid chamber 30.

When the platelet and white blood cell particles enter the fluid chamber 30, they are subjected to two opposing forces. Plasma flowing through the fluid chamber 30 with the aid of pump 80 establishes a first viscous drag force when plasma flowing through the fluid chamber 30 urges the particles toward the outlet 32. A second centrifugal force created by rotation of the rotor 12 and fluid chamber 30 acts to urge the particles toward the inlet 34.

The controller 89 regulates the rotational speed of the rotor 12 and the flow rate of the pump 80 to collect platelets and white blood cells in the fluid chamber 30. As plasma flows through the fluid chamber 30, the flow velocity of the plasma decreases and reaches a minimum as the plasma flow approaches the maximum cross-sectional area of the fluid chamber 30. Because the rotating centrifuge rotor 12 creates a sufficient gravitational field in the fluid chamber 30, the platelets accumulate near the maximum cross-sectional area of the chamber 30 rather than flowing from the chamber 30 with the plasma. The white blood cells accumulate somewhat below the maximum cross-sectional area of the chamber 30. However, density inversion tends to mix these particles slightly during this initial establishment of the saturated fluidized particle bed.

The larger white blood cells accumulate closer to inlet 34 than the smaller platelet cells, because of their different sedimentation velocities. Preferably, the rotational speed and flow rate are controlled so that very few platelets and white blood cells flow from the fluid chamber 30 during formation of the saturated fluidized particle bed.

The platelets and white blood cells continue to accumulate in the fluid chamber 30 while plasma flows through the fluid chamber 30. As the concentration of platelets increases, the interstices between the particles become reduced and the viscous drag force from the plasma flow gradually increases. Eventually the platelet bed becomes a saturated fluidized particle bed within the fluid chamber 30. Since the bed is now saturated with platelets, for each new platelet that enters the saturated bed in the fluid chamber 30, a single platelet must exit the bed. Thus, the bed operates at a steady state condition with platelets exiting the bed at a rate equal to the rate additional platelets enter the bed after flowing through inlet 34.

The saturated bed establishes itself automatically, independent of the concentration of particles flowing into the fluid chamber 30. Plasma flowing into the fluid chamber 30 passes through the platelet bed both before and after the platelet saturation point.

The saturated bed of platelets occupies a varying volume in the fluid chamber 30 near the maximum cross-sectional area of the chamber 30, depending on the flow rate and centrifugal field. The number of platelets in the saturated bed depends on a number of factors, such as the flow rate into the fluid chamber 30, the volume of the fluid chamber 30, and rotational speed. If these variables remain constant, the number of platelets in the saturated fluidized bed remains substantially constant. When the flow rate of blood components into the fluid chamber 30 changes, the bed self adjusts to maintain itself by either releasing excess platelets or accepting additional platelets flowing into the fluid chamber 30. For example, when the plasma flow rate into the fluid chamber 30 increases, this additional plasma flow sweeps excess platelets out of the now super-saturated bed, and the bed reestablishes itself in the saturated condition at the increased flow rate. Therefore, the concentration of platelets in the bed is lower due to the release of bed platelets.

After the saturated fluidized bed of platelets forms, flowing plasma carries additional platelets into the fluid chamber 30 and the bed. These additional platelets add to the bed and increase the viscous drag of the plasma flow through the bed. At some point the viscous drag is sufficient to cause platelets near the maximum cross-section area of the fluid chamber 30 to exit the saturated bed and fluid chamber 30. Thus, if the rotational speed and flow rate into the fluid chamber 30 remain constant, the number and concentration of platelets flowing into the saturated fluidized bed of platelets substantially equals the number and concentration of platelets released from the bed. This is in sharp contrast to the prior art.

Although the bed is saturated with platelets, a small number of white blood cells may be interspersed in the platelet bed. These white blood cells, however will tend to "fall" or settle out of the platelet bed toward inlet 34 due to their higher sedimentation velocity. Most white blood cells generally collect within the fluid chamber 30 between the saturated platelet bed and the inlet 34.

Red blood cells in the fluid chamber 30 also settle toward the fluid chamber inlet 34, and some of the red blood cells preferably exit the fluid chamber 30 via the inlet 34 while blood components are entering the chamber 30 via the inlet 34. In other words, bidirection flow into and out of the fluid chamber 30 may take place at the fluid chamber inlet 34.

The controller 89 preferably controls the pump 80 to limit the number of red blood cells accumulating in the fluid chamber 30. For example, the controller 89 can temporarily reverse flow of the pump 80 to cause red blood cells and other dense substances to be flushed from the fluid chamber outlet 34. In addition, the controller 89 may cycle the pump 80 to allow for accumulation of relatively sparse components, such as white blood cells, upstream the barrier 62.

The saturated fluidized bed of platelet particles formed in the fluid chamber 30 functions as a filter or barrier to white blood cells flowing into the fluid chamber 30. When blood components flow into the fluid chamber 30, plasma freely passes through the bed. However, the saturated fluidized platelet bed creates a substantial barrier to white blood cells entering the fluid chamber 30 and retains these white blood cells within the fluid chamber 30. Thus, the bed effectively filters white blood cells from the blood components continuously entering the fluid chamber 30, while allowing plasma and platelets released from the saturated bed to exit the chamber 30. This replenishment and release of platelets is referred to as the bed's self-selecting quality. Substantially all of these filtered white blood cells accumulate within the fluid chamber 30 between the saturated fluidized platelet bed and the inlet 34.

The particle separation or filtration of the saturated fluidized particle bed obviates a number of limitations associated with prior art elutriation. For example, particles may be separated or filtered in a continuous steady state manner without batch processing. In addition, an additional elutriating fluid medium is not required. Furthermore, after the saturated fluidized particle bed is established, flow rates may be varied over a range without changing the size of the particles leaving the fluid chamber 30. Unlike prior art elutriation, the present invention establishes a saturated particle bed consisting of numerically predominant particles. This bed automatically passes the predominant particles while rejecting larger particles.

The apparatus and method of the invention separate substantially all of the white blood cells from the platelets and plasma flowing through the fluid chamber 30. The barrier to white blood cells is created, at least in part, because white blood cells have a size and sedimentation velocity greater than that of the platelets forming the saturated fluidized particle bed. Therefore, particles of similar densities are separated according to different sizes or sedimentation velocities.

Because the initial separation at barrier 62 and the saturated fluidized bed remove a majority of the red blood cells and some white blood cells, the fluid exiting the fluid chamber 30 consists mainly of plasma and platelets. Unlike a conventional porous filter, where the filtered white blood cells are retained in the filter, the present invention allows a substantial fraction of white blood cells to be recovered and returned to the donor.

When the blood components are initially separated within the fluid vessel 28, a substantial number of platelets may become slightly activated. The saturated fluidized platelet bed allows white blood cells to be filtered from plasma and platelets despite this slight activation. Thus, the present invention does not require a waiting period to filter white blood cells after blood components undergo initial separation in a separation vessel 28. This is in contrast to methods using conventional filters.

After separation, the platelets and plasma exiting the fluid chamber 30 are collected in appropriate containers and stored for later use. The red blood cells and plasma removed from the vessel 28 may be combined for donor reinfusion or storage. Alternatively, these components may be further separated by the apparatus 10.

At the completion of a separation procedure, platelets in the saturated fluidized bed are harvested to recover a substantial number of platelets from the fluid chamber 30. During bed harvest, the controller 89 increases the flow rate and/or decreases the rotational speed of the rotor 12 to release platelets from the bed. This flushes from the fluid chamber 30 most of the platelets that made up the saturated fluidized bed to substantially increase platelet yield. The harvesting continues until substantially all of the platelets are removed, and just before an unacceptable number of white blood cells begin to flow from the fluid chamber 30.

The remainder of contents of the fluid chamber 30, having a high concentration of white blood cells, can be separately collected for later use or recombined with the blood components removed from vessel 28 for return to a donor.

Although the inventive device and method have been described in terms of removing white blood cells and collecting platelets, this description is not to be construed as a limitation on the scope of the invention. The invention may be used to separate any of the particle components of blood from one another. For example, the saturated fluidized bed may be formed from red blood cells to prevent flow of white blood cells through the fluid chamber 22, so long as the red blood cells do not rouleau (clump) excessively. Alternatively, the liquid for carrying the particles may be saline or another substitute for plasma. In addition, the invention may be practiced to remove white blood cells or other components from a bone marrow harvest collection or an umbilical cord cell collection harvested following birth. Another aspect the invention can be practiced to collect T cells, stem cells, or tumor cells. Further, one could practice the invention by filtering or separating particles from fluids unrelated to either blood or biologically related substances.

It will be apparent to those skilled in the art that various modifications and variations can be made to the structure and methodology of the present invention without departing from the scope or spirit of the invention. For example, the fluid chamber of the invention may be used in a separation process involving elutriation or any other particle separation means without departing from the scope of the invention. The invention, in its broadest sense, may also be used to separate many different types of particles and/ or components from one another. In addition, the above-mentioned separation vessels 28, 28a, and 28b may be generally belt shaped and have the inlet portion and outlet portion in separate ends spaced from one another without having the inlet portion connected directly to the outlet portion to form a generally annular shape. Thus, it should be understood that the invention is not limited to the examples discussed in this specification. Rather the invention is intended to cover modifications and variations provided they come within the scope of the following claims and their equivalents.

What is claimed is:

1. A tubing set for use with a centrifuge having a rotor rotatable about an axis of rotation, the rotor including a retainer, the tubing set comprising:

a separation vessel for placement in the retainer, the vessel including an inlet end portion including an inlet port for supplying to the vessel a fluid to be separated into components, an outlet end portion including at least a first collection port, a second collection port, and a third collection port for removing separated components of the fluid from the vessel, and a flow path extending between the inlet end portion and the outlet end portion;

an inlet line fluidly coupled to the inlet port;

a first collection line fluidly coupled to the first collection port;

a second collection line fluidly coupled to the second collection port;

a third collection line fluidly coupled to the third collection port;

a fluid chamber for separating components of the fluid after initial separation in the vessel, the fluid chamber being capable of being mounted on the rotor and including a fluid chamber inlet fluidly coupled to the first collection line, a fluid chamber outlet, and a fluid chamber wall extending between and defining the fluid chamber inlet and the fluid chamber outlet, the fluid chamber wall having an inner surface defining an interior having a maximum cross-sectional area at a position between the fluid chamber inlet and the fluid chamber outlet, the interior converging from the position of the maximum cross-sectional area toward the fluid chamber inlet and converging from the position of the maximum cross-sectional area toward the fluid chamber outlet; and an outflow line fluidly coupled to the fluid chamber outlet.

2. The tubing set of claim 1, further comprising a fourth collection port in the outlet end portion of the vessel and a fourth collection line fluidly coupled to the fourth collection port, wherein the fourth collection port adjusts an interface of separated components of the fluid in the vessel.

3. The tubing set of claim 1, further comprising a barrier in the outlet end portion of the vessel for substantially blocking flow of at least a first component of the fluid, the first port being between the barrier and the inlet end portion of the vessel to remove the blocked first component of the fluid.

4. The tubing set of claim 3, wherein the barrier is a skimmer dam extending across the vessel, and wherein the outlet end portion of the vessel includes a first passage for at least a relatively low density component of the fluid and a second passage for at least a relatively high density component of the fluid, the skimmer dam being between the first and second passages such that the first passage is closer to the axis of rotation than the second passage when the vessel is placed in the retainer.

5. The tubing set of claim 3, wherein at least the outlet end portion of the vessel is formed of at least one of a semi-rigid material and a flexible material so that at least one ridge in the retainer forms the barrier in the outlet end portion of the vessel.

6. The tubing set of claim 3, wherein the vessel includes a first wall and a second wall spaced apart from one another to define the flow path therebetween, the outlet end portion including two sealed portions wherein the first wall and the second wall are sealed together to define a flow passage between the sealed portions, the sealed portions being upstream the barrier so that the flow passage directs flow of the components of the fluid toward the barrier.

7. The tubing set of claim 1, wherein at least the outlet end portion of the vessel is formed of at least one of a semi-rigid material and a flexible material and includes a first wall for facing the axis of rotation and a second wall spaced from the first wall to define the flow path therebetween, the outlet end portion including at least one sealed portion wherein the first wall and the second wall are sealed together, the sealed portion being between top and bottom edges of the vessel to form at least first and second passages in the outlet end portion.

8. The tubing set of claim 7, wherein the vessel further includes at least a first support on the first wall adjacent to the first passage and a second support on the second wall adjacent to the second passage, the first support forming a first dam in the vessel for facing away from the axis of rotation and the second support forming a second dam for facing toward the axis of rotation, and wherein when the vessel is placed in the retainer, the first and second dams form a barrier for substantially blocking flow of at least a first component of the fluid and the first passage is positioned further away from the axis of rotation than the second passage.

9. The tubing set of claim 8, further comprising an elongate member passing through the sealed portion, a first portion of the elongate member providing the first support and a second portion of the elongate member providing the second support.

10. The tubing set of claim 1, wherein the outlet end portion of the vessel includes a first wall for facing the axis of rotation and a second wall spaced from the first wall, the first wall including a trap dam extending toward the second wall to trap relatively low density substances, the trap dam being between the inlet end portion of the vessel and the first collection port.

11. The tubing set of claim 1, wherein the vessel is a generally annular channel including an inner wall for facing the axis of rotation and an outer wall spaced from the inner wall to define the flow path therebetween, the second collection port being closer to the inner wall than the first and third collection ports to collect at least a relatively low density component of the fluid, and the third collection port being further from the inner wall than the first and second collection ports to collect at least a relatively high density component of the fluid.

12. The tubing set of claim 1, wherein the fluid chamber includes at least one groove formed on the interior of the fluid chamber, the groove reducing Coriolis jetting of components of the fluid entering the fluid chamber interior through the fluid chamber inlet.

13. The tubing set of claim 1, wherein the fluid chamber includes at least one step formed on the interior of the fluid chamber, the step reducing Coriolis jetting of components of the fluid entering the fluid chamber interior through the fluid chamber inlet.

14. A centrifugal separation apparatus comprising:

a separation vessel including a first wall and a second wall formed of at least one of a flexible material and a semi-rigid material, inner surfaces of the first and second walls being spaced from one another to define a flow path therebetween for a fluid capable of being separated into components, the vessel including an inlet portion having an inlet port for introducing the fluid into the vessel, and an outlet portion spaced from the inlet portion and having a collection port for removing at least one separated component of the fluid from the vessel, the outlet portion including at least one sealed portion wherein the first and second walls are sealed together, the sealed portion being located between top and bottom edges of the vessel to form at least first and second flow passages in the outlet portion, the sealed portion defining at least a portion of a barrier for the at least one separated fluid component when the separation vessel is placed in a retainer on a centrifuge rotor;

a first support on the first wall adjacent to the first passage; and a second support on the second wall adjacent to the second passage, the first support and the second support forming a pair of dams in the vessel, the sealed portion being between the pair of dams so that the pair of dams and sealed portion form the barrier.

15. The centrifugal separation apparatus of claim 14, further comprising an elongate member passing through the sealed portion, a first portion of the elongate member providing the first support and a second portion of the elongate member providing the second support.

16. A centrifugal separation apparatus comprising:

a separation vessel including a first wall and a second wall formed of at least one of a flexible material and a semi-rigid material, inner surfaces of the first and second walls being spaced from one another to define a flow path therebetween for a fluid capable of being separated into components, the vessel including an inlet portion having an inlet port for introducing the fluid into the vessel, and an outlet portion spaced from the inlet portion and having a collection port for removing at least one separated component of the fluid from the vessel, the outlet portion including a first sealed portion wherein the first and second walls are sealed together, and a second sealed portion wherein the first and second walls are sealed together, the first and second sealed portions being spaced from one another and from the top and bottom edges of the vessel to form a first flow passage between the first sealed portion and a top edge of the vessel, a second flow passage between the first and second sealed portions, and a third flow passage between the second sealed portion and a bottom edge of the vessel, the first and second sealed portions defining at least a portion of a barrier for the at least one separated fluid component when the separation vessel is placed in a retainer on a centrifuge rotor.

17. The centrifugal separation apparatus of claim 16, further comprising an elongate member passing through the first sealed portion and the second sealed portion, a first portion of the elongate member being adjacent to the first flow passage and forming a first dam in the vessel, a second portion of the elongate member being adjacent to the second flow passage and forming a second dam in the vessel, and a third portion of the elongate member being adjacent to the third flow passage and forming a third dam in the vessel, the first and second sealed portions and the first, second, and third dams forming the barrier.

18. The centrifugal separation apparatus of claim 16, wherein the outlet portion further includes third and fourth sealed portions defining a restricted flow passage therebetween, the restricted flow passage being between the barrier and the inlet portion of the vessel to guide components of the fluid toward the barrier.

19. A centrifugal separation apparatus comprising:

a separation vessel including a first wall and a second wall formed of at least one of a flexible material and a semi-rigid material, inner surfaces of the first and second walls being spaced from one another to define a flow path therebetween for a fluid capable of being separated into components, the vessel including an inlet portion having an inlet port for introducing the fluid into the vessel, and an outlet portion spaced from the inlet portion and having a collection port for removing at least one separated component of the fluid from the vessel, the outlet portion including at least one sealed portion wherein the first and second walls are sealed together, the sealed portion being located between top and bottom edges of the vessel to form at least first and second flow passages in the outlet portion, the sealed portion defining at least a portion of a barrier for the at least one separated fluid component when the separation vessel is placed in a retainer on a centrifuge rotor; and a fluid chamber for separating components of the fluid initially separated in the vessel, the fluid chamber including a fluid chamber inlet fluidly coupled to the collection port, a fluid chamber outlet, and a fluid chamber wall extending between and defining the fluid chamber inlet and the fluid chamber outlet, the fluid chamber wall having an inner surface defining an interior having a maximum cross-sectional area at a position between the fluid chamber inlet and the fluid chamber outlet, the interior converging from the position of the maximum cross-sectional area toward the fluid chamber inlet and converging from the position of the maximum cross-sectional area toward the fluid chamber outlet.

20. A centrifugal separation apparatus comprising:

a rotor configured to be connected to a motor for rotation about an axis of rotation;

a retainer on the rotor for receiving a separation vessel therein, the retainer including an inner wall spaced from the axis of rotation and an outer wall spaced further from the axis of rotation than the inner wall, the inner wall and the outer wall defining a groove therebetween;

a first ridge extending from one of the inner wall and the outer wall; and a second ridge extending from the other of the inner wall and the outer wall, the first and second ridges being positioned across from one another and the first ridge being above the second ridge in the direction of the axis of rotation, so that when the separation vessel is placed in the retainer, the first ridge forms a first dam in the vessel and the second ridge forms a second dam in the vessel, the first and second dams cooperating to form a barrier for substantially blocking passage of predetermined particles in the vessel while allowing passage of other particles and liquid.

21. The centrifugal separation apparatus of claim 20, further comprising a third ridge extending from the one of the inner wall and the outer wall from which the second ridge extends, the third ridge being positioned across from the first ridge and above the first ridge, so that when the separation vessel is placed in the retainer the third ridge forms a third dam cooperating with the first and second dams to form the barrier.

22. The centrifugal separation apparatus of claim 20, further comprising a third ridge positioned on the inner wall at a location spaced from the first and second ridges, the third ridge forming a trap dam for trapping low density substances along an inner portion of the vessel.

23. The centrifugal separation apparatus of claim 20, wherein a substantial portion of the groove is curved and has a constant radius of curvature.

24. The centrifugal separation apparatus of claim 20, further comprising a fluid chamber holder for holding a fluid chamber on the rotor so that an outlet of the fluid chamber is closer to the axis of rotation than an inlet of the fluid chamber.

25. The centrifugal separation apparatus of claim 20, wherein the separation vessel is a generally annular channel formed of at least one of a semi-rigid material and a flexible material, and wherein the groove is generally annular.

26. A centrifugal separation apparatus comprising:
   a centrifuge rotor configured to be rotated by a motor about an axis of rotation;
   a retainer on the centrifuge rotor; and
   a separation vessel in the retainer, the vessel including
      an inlet portion including an inlet port for supplying to the vessel a fluid to be separated into components,
      an outlet portion including
         a barrier for substantially blocking passage of at least one of the separated components of the fluid,
         at least one collection port between the barrier and the inlet portion of the vessel for removing at least the blocked component of the fluid from the vessel, and
         a first passage for a relatively low density component of the fluid and a second passage for a relatively high density component of the fluid, the barrier being between the first and second passages and the first passage being closer to the axis of rotation than the second passage,
      a flow path extending between the inlet end portion and the outlet end portion, and
      a trap dam between the collection port and the inlet portion, the trap dam extending away from the axis of rotation to trap a portion of a low density substance along an inner portion of the vessel.

27. The centrifugal separation apparatus of claim 26, wherein at least a part of the vessel is formed of at least one of a semi-rigid material and a flexible material, and wherein the retainer includes an inner wall spaced from the axis of rotation and an outer wall spaced further from the axis of rotation than the inner wall, the inner and outer walls defining a groove therebetween for receiving the vessel, the inner wall of the retainer including a ridge extending toward the outer wall, the ridge deforming the vessel to form the trap dam in the vessel.

28. The centrifugal separation apparatus of claim 26, wherein at least the outlet portion of the vessel is formed of at least one of a semi-rigid material and a flexible material, and wherein the retainer includes an inner wall spaced from the axis of rotation and an outer wall spaced further from the axis of rotation than the inner wall of the retainer, the inner and outer walls defining a groove therebetween for receiving the vessel, the apparatus further comprising
   a first ridge extending from one of the inner wall and the outer wall, and
   a second ridge extending from the other of the inner wall and the outer wall, the first and second ridges being across from one another and the first ridge being above the second ridge, the first and second ridges deforming the vessel to form the barrier.

29. The centrifugal separation apparatus of claim 26, wherein at least the outlet portion of the vessel is formed of at least one of a semi-rigid material and a flexible material, and wherein the retainer includes an inner wall spaced from the axis of rotation and an outer wall spaced further from the axis of rotation than the inner wall of the retainer, the inner and outer walls defining a groove therebetween for receiving the vessel, the apparatus further comprising
   a first support between the vessel and the inner wall of the retainer, and
   a second support between the vessel and the outer wall of the retainer, the first and second supports deforming the vessel to form the barrier.

30. The centrifugal separation apparatus of claim 26, wherein the outlet portion of the vessel includes a first wall facing the axis of rotation and a second wall spaced from the inner wall to define the flow path therebetween, the outlet portion including at least one sealed portion wherein the first wall and the second wall are sealed together, the sealed portion being between top and bottom edges of the vessel to form the first and second passages.

31. The centrifugal separation apparatus of claim 26, further comprising a fluid chamber on the rotor for separating components of the fluid initially separated in the vessel, the fluid chamber including a fluid chamber inlet fluidly coupled to the collection port, a fluid chamber outlet, and a fluid chamber wall extending between and defining the fluid chamber inlet and the fluid chamber outlet, the fluid chamber wall having an inner surface defining an interior having a maximum cross-sectional area at a position between the fluid chamber inlet and the fluid chamber outlet, the interior converging from the position of the maximum cross-sectional area toward the fluid chamber inlet and converging from the position of the maximum cross-sectional area toward the fluid chamber outlet.

32. A centrifugal separation apparatus comprising:
   a centrifuge rotor configured to be rotated by a motor about an axis of rotation;
   a retainer on the centrifuge rotor;
   a separation vessel in the retainer, the vessel including
      an inlet portion including an inlet port for supplying to the vessel a fluid to be separated into components,
      an outlet portion including
         a barrier for substantially blocking passage of at least one of the separated components of the fluid,
         at least one collection port between the barrier and the inlet portion of the vessel for removing at least the blocked component of the fluid from the vessel, and
         a first passage for a relatively low density component of the fluid and a second passage for a relatively high density component of the fluid, the barrier being between the first and second passages and the first passage being closer to the axis of rotation than the second passage, and
      a flow path extending between the inlet end portion and the outlet end portion;
   a fluid chamber holder on the centrifuge rotor; and
   a fluid chamber in the holder for separating components of the fluid initially separated in the vessel, the fluid chamber including a fluid chamber inlet fluidly coupled to collection port, a fluid chamber outlet, and a fluid chamber wall extending between and defining the fluid chamber inlet and the fluid chamber outlet, the fluid chamber wall having an inner surface defining an interior having a maximum cross-sectional area at a position between the fluid chamber inlet and the fluid chamber outlet, the interior converging from the posi- tion of the maximum cross-sectional area toward the fluid chamber inlet and converging from the position of the maximum cross-sectional area toward the fluid chamber outlet.

33. The centrifugal separation apparatus of claim 32, wherein the fluid chamber includes at least one groove formed on the interior of the fluid chamber, the groove reducing Coriolis jetting of components of the fluid entering the fluid chamber interior through the fluid chamber inlet.

34. The centrifugal separation apparatus of claim 32, wherein the fluid chamber includes at least one step formed on the interior of the fluid chamber, the step reducing Coriolis jetting of components of the fluid entering the fluid chamber interior through the fluid chamber inlet.

35. The centrifugal separation apparatus of claim 32, wherein at least the outlet portion of the vessel is formed of at least one of a semi-rigid material and a flexible material, and wherein the retainer includes an inner wall spaced from the axis of rotation and an outer wall spaced further from the axis of rotation than the inner wall of the retainer, the inner and outer walls forming a groove therebetween for receiving the vessel, the apparatus further comprising a ridge positioned on the inner wall at a location spaced from the barrier, the ridge forming a trap dam for trapping low density substances along an inner portion of the vessel.

36. The centrifugal separation apparatus of claim 32, wherein at least the outlet portion of the vessel is formed of at least one of a semi-rigid material and a flexible material, and wherein the retainer includes an inner wall spaced from the axis of rotation and an outer wall spaced further from the axis of rotation than the inner wall of the retainer, the inner and outer walls defining a groove therebetween for receiving the vessel, the apparatus further comprising a first ridge extending from one of the inner wall and the outer wall, and a second ridge extending from the other of the inner wall and the outer wall, the first and second ridges being across from one another and the first ridge being above the second ridge, the first and second ridges deforming the vessel to form the barrier.

37. The centrifugal separation apparatus of claim 32, wherein at least the outlet portion of the vessel is formed of at least one of a semi-rigid material and a flexible material, and wherein the retainer includes an inner wall spaced from the axis of rotation and an outer wall spaced further from the axis of rotation than the inner wall of the retainer, the inner and outer walls defining a groove therebetween for receiving the vessel, the apparatus further comprising a first support between the vessel and the inner wall of the retainer, and a second support between the vessel and the outer wall of the retainer, the first and second supports deforming the vessel to form the barrier.

38. The centrifugal separation apparatus of claim 32, wherein the outlet portion of the vessel includes a first wall facing the axis of rotation and a second wall spaced from the inner wall to define the flow path therebetween, the outlet portion including at least one sealed portion wherein the first wall and the second wall are sealed together, the sealed portion being between top and bottom edges of the vessel to form the first and second passages.

39. The centrifugal separation apparatus of claim 32, wherein the vessel includes an interface positioning port for removing components of the fluid from the vessel.

40. A method of separating at least first and second particles, the first particles being less dense than the second particles, comprising introducing into a vessel liquid carrying at least the first and second particles, the vessel including an outlet portion having a barrier and a collection port in fluid communication with a fluid chamber;

rotating the vessel and the fluid chamber about an axis of rotation so that the first and second particles form respective stratified layers in the vessel;

blocking passage of at least the first particles in the vessel with the barrier while allowing at least some of the liquid and second particles to flow past the barrier;

removing via the collection port the blocked first particles and at least some of the second particles and the liquid;

passing the first particles, the second particles, and the liquid from the collection port to the fluid chamber;

forming a saturated fluidized particle bed of the first particles in the fluid chamber; and filtering second particles with the saturated fluidized bed while allowing the liquid and at least some of first particles to flow out of the fluid chamber.

41. The method of claim 40, wherein the liquid is plasma, the first particles are platelets, the second particles are white blood cells, and wherein the plasma also carries red blood cells.

42. The method of claim 40, wherein the vessel defines a flow path having a trap dam extending away from the axis of rotation, and the method further comprises introducing a priming fluid in the vessel, trapping a portion of the priming fluid upstream the trap dam, and causing the liquid to flow around the trap dam and carry the first particles toward the collection port.

43. The method of claim 40, further comprising replacing at least part of the trapped portion of the priming fluid with the liquid.

44. The method of claim 40, wherein the liquid also carries third particles and the passing includes flowing the liquid and first, second, and third particles into the fluid chamber via a port in the fluid chamber, the method further comprising allowing flow of the third particles from the fluid chamber via the port during the passing.

45. The method of claim 44, wherein the liquid is plasma, the first particles are platelets, the second particles are white blood cells, and the third particles are red blood cells.

46. A method of separating components of a fluid, comprising introducing into a vessel a priming fluid, the vessel defining a flow passage having a trap dam and a barrier;

rotating the vessel about an axis of rotation to trap a portion of the priming fluid upstream the trap dam;

passing into the vessel a fluid to be separated;

allowing the components of the fluid to separate in the vessel according to density differences;

accumulating at least a relatively intermediate density component of the fluid upstream the barrier while allowing relatively higher and lower density components of the fluid to flow past the barrier;

guiding, with the trapped priming fluid, flow of the intermediate density component toward the barrier; and removing the accumulated intermediate density component from the vessel.

47. The method of claim 46, further comprising replacing at least part of the trapped portion of the priming fluid with a relatively low density component of the separated fluid.

48. The method of claim 46, wherein the fluid of the passing step includes blood components.

* * * * *